United States Patent
Izhar et al.

(10) Patent No.: US 12,168,062 B2
(45) Date of Patent: Dec. 17, 2024

(54) GUIDE RNA THAT TARGETS A MUTANT HUMAN GUANYLATE CYCLASE 2A ALLELE

(71) Applicant: EmendoBio Inc., Wilmington, DE (US)

(72) Inventors: Lior Izhar, Tel Aviv (IL); David Baram, Nir Zvi (IL); Joe Georgeson, Rehevot (IL); Michal Golan-Mashiach, Ness-Ziona (IL); Asael Herman, Ness-Ziona (IL); Rafi Emmanuel, Ramla (IL)

(73) Assignee: EmendoBio Inc., Wilmington, DE (US)

( * ) Notice: Subject to any disclaimer, the term of this patent is extended or adjusted under 35 U.S.C. 154(b) by 0 days.

(21) Appl. No.: 16/203,004

(22) Filed: Nov. 28, 2018

(65) Prior Publication Data
US 2023/0173106 A1    Jun. 8, 2023

Related U.S. Application Data

(60) Provisional application No. 62/680,479, filed on Jun. 4, 2018, provisional application No. 62/591,333, filed on Nov. 28, 2017.

(51) Int. Cl.
| | |
|---|---|
| *C12N 15/11* | (2006.01) |
| *A61K 48/00* | (2006.01) |
| *A61P 27/00* | (2006.01) |
| *C12N 9/22* | (2006.01) |
| *C12N 15/113* | (2010.01) |

(52) U.S. Cl.
CPC .......... *A61K 48/0066* (2013.01); *A61P 27/00* (2018.01); *C12N 9/22* (2013.01); *C12N 15/11* (2013.01); *C12N 15/113* (2013.01); *C12N 15/1137* (2013.01); *C12Y 301/00* (2013.01)

(58) Field of Classification Search
CPC .......... C12N 15/113; C12N 9/22; A61P 27/00
USPC ........................................................ 514/44
See application file for complete search history.

(56) References Cited

FOREIGN PATENT DOCUMENTS

| | | |
|---|---|---|
| WO | PCT/US18/62871 | 11/2018 |
| WO | PCT/US19/23715 | 3/2019 |

OTHER PUBLICATIONS

Payne (J Med Genetics, 2001, vol. 38, p. 611-647).*
Mukherjee (Eye, 2014, vol. 28, p. 481-487).*
Sun (Ophthalmic Genetics, 2020, vol. 41, No. 6, p. 548-555).*
Jinke (Science, 2012, vol. 337, p. 816-821).*
Turk, 2017, "Similar editing efficiency with 2-part and single guide RNA".*
Christie (Mol. Therapy, 2020, vol. 28, No. 8, p. 1846-1857.*
U.S. Appl. No. 16/202,955, filed Nov. 28, 2018, Izhar.
U.S. Appl. No. 16/202,867, filed Nov. 28, 2018, Izhar.
U.S. Appl. No. 16/203,056, filed Nov. 28, 2018, Izhar.
U.S. Appl. No. 16/203,094, filed Nov. 28, 2018, Izhar.
U.S. Appl. No. 16/203,134, filed Nov. 28, 2018, Izhar.
U.S. Appl. No. 16/203,169, filed Nov. 28, 2018, Izhar.
U.S. Appl. No. 16/203,231, filed Nov. 28, 2018, Izhar.
Burstein et al. (2017), "New CRISPR-Cas systems from uncultivated microbes," Nature 542:237-41.
Sentmanat et al. (2018), "A Survey of Validation Strategies for CRISPR-Cas9 Editing," Scientific Reports 8:888, doi: 10.1038/s41598-018-19441-8.
Zuris et al. (2015), "Cationic lipid-mediated delivery of proteins enables efficient protein based genome editing in vitro and in vivo," Nat Biotechnol. 33(1):73-80.
Buch et al., "AAV-mediated gene therapy for retinal disorders: from mouse to man" Gene Therapy (2008) 15, 849-857.
Han Z et al. (2012), "Comparative Analysis of DNA Nanoparticles and AAVs for Ocular Gene Delivery" PLoS One 7(12): e52189.
Ralph et al., "Gene therapy for neurodegenerative and ocular diseases using lentiviral vectors" Clinical Science (2006), 110, 37-46.
Wang et al. J. "Lipid Nanoparticles for Ocular Gene Therapy" Funct. Biomater. 2015, 6, 379-394.

* cited by examiner

*Primary Examiner* — Michael C Wilson
(74) *Attorney, Agent, or Firm* — Potomac Law Group, PLLC; Jamaica Szeliga

(57) ABSTRACT

RNA molecules comprising a guide sequence portion having 17-20 nucleotides in the sequence of 17-20 contiguous nucleotides set forth in any one of SEQ ID NOs: 1-3010 and compositions, methods, and uses thereof.

6 Claims, No Drawings

Specification includes a Sequence Listing.

GUIDE RNA THAT TARGETS A MUTANT HUMAN GUANYLATE CYCLASE 2A ALLELE

This application claims the benefit of U.S. Provisional Application No. 62/680,479, filed Jun. 4, 2018 and U.S. Provisional Application No. 62/591,333, filed Nov. 28, 2017, the contents of each of which are hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference nucleotide sequences which are present in the filed named "210702 90237-A_SubstituteSequenceListing_DH. txt", which is 551 kilobytes in size, and which was created on Jun. 30, 2021 in the IBM-PC machine format, having an operating system compatibility with MS-Windows, which is contained in the text file filed Jul. 2, 2021 as part of this application.

BACKGROUND OF INVENTION

There are several classes of DNA variation in the human genome, including insertions and deletions, differences in the copy number of repeated sequences, and single nucleotide polymorphisms (SNPs). A SNP is a DNA sequence variation occurring when a single nucleotide (adenine (A), thymine (T), cytosine (C), or guanine (G)) in the genome differs between human subjects or paired chromosomes in an individual. Over the years, the different types of DNA variations have been the focus of the research community either as markers in studies to pinpoint traits or disease causation or as potential causes of genetic disorders.

A genetic disorder is caused by one or more abnormalities in the genome. Genetic disorders may be regarded as either "dominant" or "recessive." Recessive genetic disorders are those which require two copies (i.e., two alleles) of the abnormal/defective gene to be present. In contrast, a dominant genetic disorder involves a gene or genes which exhibit(s) dominance over a normal (functional/healthy) gene or genes. As such, in dominant genetic disorders only a single copy (i.e., allele) of an abnormal gene is required to cause or contribute to the symptoms of a particular genetic disorder. Such mutations include, for example, gain-of-function mutations in which the altered gene product possesses a new molecular function or a new pattern of gene expression. Other examples include dominant negative mutations, which have a gene product that acts antagonistically to the wild-type allele.

Cone Rod Dystrophy

The cone-rod dystrophies (CORD) are a heterogeneous group of progressive genetically determined retinal disorders, which may be inherited as an autosomal dominant, autosomal recessive, or X-linked trait. Typically, they are characterized clinically by a loss of visual acuity, abnormal color vision, photophobia, and visual field loss and may develop macular atrophy. Mutations in the gene 'Guanylate cyclase 2D, membrane (retina-specific)' (GUCY2D) have been demonstrated to be associated with an autosomal dominant CORD.

SUMMARY OF THE INVENTION

Disclosed is an approach for knocking out the expression of a dominant-mutated allele by disrupting the dominant-mutated allele or degrading the resulting mRNA.

The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutated allele"), and the other allele encoding for a functional protein ("functional allele"). In some embodiments, the method further comprises the step of knocking out expression of the mutated protein and allowing expression of the functional protein.

According to embodiments of the present invention, there is provided a first RNA molecule comprising a guide sequence portion having 17-20 nucleotides in the sequence of 17-20 contiguous nucleotides set forth in any one of SEQ ID NOs: 1-3010.

According to embodiments of the present invention, there is provided a first RNA molecule comprising a guide sequence portion having 17-20 contiguous nucleotides set forth in any one of SEQ ID NOs: 1-3010.

According to some embodiments of the present invention, there is provided a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a method for inactivating a mutant GUCY2D allele in a cell, the method comprising delivering to the cell a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a method for treating CORD, the method comprising delivering to a subject having CORD a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-3010 and a CRISPR nuclease for inactivating a mutant GUCY2D allele in a cell, comprising delivering to the cell the composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to embodiments of the present invention, there is provided a medicament comprising an RNA molecule comprising a guide sequence portion having 17-20 nucleotides in the sequence of 17-20 contiguous nucleotides set forth in any one of SEQ ID NOs: 1-3010 and a CRISPR nuclease for use in inactivating a mutant GUCY2D allele in a cell, wherein the medicament is administered by delivering to the cell the composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-3010 and a CRISPR nuclease for treating ameliorating or preventing CORD, comprising delivering to a subject having or at risk of having CORD the composition of comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a medicament comprising the composition comprising an RNA molecule comprising a guide sequence portion having 17-20 nucleotides in the sequence of 17-20 contiguous nucleotides set forth in any one of SEQ ID NOs: 1-3010 and a CRISPR nuclease for use in treating ameliorating or preventing CORD, wherein the medicament is administered by delivering to a subject having or at risk of having CORD the composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a kit for inactivating a mutant GUCY2D allele in a cell, comprising an RNA molecule comprising a guide sequence portion having 17-20 nucleotides in the sequence of 17-20 contiguous nucleotides set forth in any one of SEQ ID NOs: 1-3010, a CRISPR nuclease, and/or a tracrRNA molecule; and instructions for delivering the RNA molecule; CRISPR nuclease, and/or the tracrRNA to the cell.

According to some embodiments of the present invention, there is provided a kit for treating CORD in a subject, comprising an RNA molecule comprising a guide sequence portion having 17-20 nucleotides in the sequence of 17-20 contiguous nucleotides set forth in any one of SEQ ID NOs: 1-3010, a CRISPR nuclease, and/or a tracrRNA molecule; and instructions for delivering the RNA molecule; CRISPR nuclease, and/or the tracrRNA to a subject having or at risk of having CORD.

DETAILED DESCRIPTION

Definitions

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The "guide sequence portion" of an RNA molecule refers to a nucleotide sequence that is capable of hybridizing to a specific target DNA sequence, e.g., the guide sequence portion has a nucleotide sequence which is fully complementary to said target DNA sequence. In some embodiments, the guide sequence portion is 17, 18, 19, 20, 21, 22, 23, or 24 nucleotides in length, or approximately 17-24, 18-22, 19-22, 18-20, or 17-20 nucleotides in length. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence.

In embodiments of the present invention, an RNA molecule comprises a guide sequence portion having 17-20 nucleotides in the sequence of 17-20 contiguous nucleotides set forth in any one of SEQ ID NOs: 1-3010, 1-742, or 743-3010.

As used herein, "contiguous nucleotides" set forth in a SEQ ID NO refers to nucleotides in a sequence of nucleotides in the order set forth in the SEQ ID NO without any intervening nucleotides.

In embodiments of the present invention, the guide sequence portion may be 20 nucleotides in length and consists of 20 nucleotides in the sequence of 20 contiguous nucleotides set forth in any one of SEQ ID NOs: 1-3010. In embodiments of the present invention, the guide sequence portion may be less than 20 nucleotides in length. For example, in embodiments of the present invention the guide sequence portion may be 17, 18, or 19 nucleotides in length. In such embodiments the guide sequence portion may consist of 17, 18, or 19 nucleotides, respectively, in the sequence of 17-20 contiguous nucleotides set forth in any one of SEQ ID NOs: 1-3010. For example, a guide sequence portion having 17 nucleotides in the sequence of 17 contiguous nucleotides set forth in SEQ ID NO: 1 may consist of any one of the following nucleotide sequences (nucleotides excluded from the contiguous sequence are marked in strike-through):

SEQ ID NO: 1
UGUGCUUCUCCUUAGGGUCU 17 nucleotide guide sequence 1:
~~UGU~~ GCUUCUCCUUAGGGUCU 17 nucleotide guide sequence 2:
~~UG~~ UGCUUCUCCUUAGGGUC ~~U~~

17 nucleotide guide sequence 3:
~~U~~ GCUUCUCCUUAGGGU ~~CU~~

17 nucleotide guide sequence 4:
UGUGCUUCUCCUUAGGG ~~UCU~~

In embodiments of the present invention, the guide sequence portion may be greater than 20 nucleotides in length. For example, in embodiments of the present invention the guide sequence portion may be 21, 22, 23, or 24 nucleotides in length. In such embodiments the guide sequence portion comprises 20 nucleotides in the sequence of 20 contiguous nucleotides set forth in any one of SEQ ID NOs: 1-3010 and additional nucleotides fully complimentary to a nucleotide or sequence of nucleotides adjacent to the 3' end of the target sequence, 5' end of the target sequence, or both.

In embodiments of the present invention a CRISPR nuclease and an RNA molecule comprising a guide sequence portion form a CRISPR complex that binds to a target DNA sequence to effect cleavage of the target DNA sequence. CRISPR nucleases, e.g. Cpf1, may form a CRISPR complex comprising a CRISPR nuclease and RNA molecule without a further tracrRNA molecule. Alternatively, CRISPR nucleases, e.g. Cas9, may form a CRISPR complex between the CRISPR nuclease, an RNA molecule, and a tracrRNA molecule.

In embodiments of the present invention, the RNA molecule may further comprise the sequence of a tracrRNA molecule. Such embodiments may be designed as a synthetic fusion of the guide portion of the RNA molecule and the trans-activating crRNA (tracrRNA). (See Jinek (2012) Science). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via basepairing and may be advantageous in certain applications of the invention described herein.

The term "tracr mate sequence" refers to a sequence sufficiently complementary to a tracrRNA molecule so as to hybridize to the tracrRNA via basepairing and promote the formation of a CRISPR complex. (See e.g., U.S. Pat. No. 8,906,616). In embodiments of the present invention, the RNA molecule may further comprise a portion having a tracr mate sequence.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity. Gene modification can be achieved using a nuclease, for example a CRISPR nuclease.

Embodiments

The present disclosure provides a method for utilizing at least one naturally occurring nucleotide difference or polymorphism (e.g., single nucleotide polymorphism (SNP)) for distinguishing/discriminating between two alleles of a gene, one allele bearing a mutation such that it encodes a mutated protein causing a disease phenotype ("mutated allele"), and the other allele encoding for a functional protein ("functional allele"). The method further comprises the step of knocking out expression of the mutated protein and allowing expression of the functional protein. In some embodiments, the method is for treating, ameliorating, or preventing a dominant negative genetic disorder.

According to embodiments of the present invention, there is provided a first RNA molecule comprising a guide sequence portion having 17-20 nucleotides in the sequence of 17-20 contiguous nucleotides set forth in any one of SEQ ID NOs: 1-3010.

According to embodiments of the present invention, there is provided a first RNA molecule comprising a guide sequence portion having 17-20 contiguous nucleotides set forth in any one of SEQ ID NOs: 1-3010.

According to embodiments of the present invention, an RNA molecule may further comprise a portion having a sequence which binds to a CRISPR nuclease.

According to embodiments of the present invention, the sequence which binds to a CRISPR nuclease is a tracrRNA sequence.

According to embodiments of the present invention, an RNA molecule may further comprise a portion having a tracr mate sequence.

According to embodiments of the present invention, an RNA molecule may further comprise one or more linker portions.

According to embodiments of the present invention, an RNA molecule may be up to 300, 290, 280, 270, 260, 250, 240, 230, 220, 210, 200, 190, 180, 170, 160, 150, 140, 130, 120, 110, or 100 nucleotides in length. Each possibility represents a separate embodiment. In embodiments of the present invention, the RNA molecule may be 17 up to 300 nucleotides in length, 100 up to 300 nucleotides in length, 150 up to 300 nucleotides in length, 200 up to 300 nucleotides in length, 100 to 200 nucleotides in length, or 150 up to 250 nucleotides in length. Each possibility represents a separate embodiment.

According to some embodiments of the present invention, there is provided a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to embodiments of the present invention, the composition may comprise a second RNA molecule comprising a guide sequence portion.

According to embodiments of the present invention, the guide sequence portion of the second RNA molecule comprises 17-20 nucleotides in the sequence of 17-20 contiguous nucleotides set forth in any one of SEQ ID NOs: 1-3010.

According to embodiments of the present invention, the 17-20 nucleotides of the guide sequence portion of the second RNA molecule are in a different sequence from the sequence of the guide sequence portion of the first RNA molecule Embodiments of the present invention may comprise a tracrRNA molecule.

According to some embodiments of the present invention, there is provided a method for inactivating a mutant GUCY2D allele in a cell, the method comprising delivering to the cell a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a method for treating CORD, the method comprising delivering to a subject having CORD a composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to embodiments of the present invention, the composition comprises a second RNA molecule comprising a guide sequence portion having 17-20 nucleotides in the sequence of 17-20 contiguous nucleotides set forth in any one of SEQ ID NOs: 1-3010.

According to embodiments of the present invention, the 17-20 nucleotides of the guide sequence portion of the second RNA molecule are in a different sequence from the sequence of the guide sequence portion of the first RNA molecule According to embodiments of the present invention, the CRISPR nuclease and the RNA molecule or RNA molecules are delivered to the subject and/or cells substantially at the same time or at different times.

According to embodiments of the present invention, the tracrRNA is delivered to the subject and/or cells substantially at the same time or at different times as the CRISPR nuclease and RNA molecule or RNA molecules.

According to embodiments of the present invention, the first RNA molecule targets a SNP or disease-causing mutation in an exon or promoter of a mutated allele, and wherein the second RNA molecule targets a SNP in the same or a different exon of the mutated allele, a SNP in an intron, or a sequence in an intron present in both the mutated or functional allele.

According to embodiments of the present invention, the first RNA molecule or the first and the second RNA molecules target a SNP in the promoter region, the start codon, or the untranslated region (UTR) of a mutated allele.

According to embodiments of the present invention, the first RNA molecule or the first and the second RNA molecules targets at least a portion of the promoter and/or the start codon and/or a portion of the UTR of a mutated allele.

According to embodiments of the present invention, the first RNA molecule targets a portion of the promoter, a first SNP in the promoter, or a SNP upstream to the promoter of a mutated allele and the second RNA molecule is targets a second SNP, which is downstream of the first SNP, and is in the promoter, in the UTR, or in an intron or in an exon of a mutated allele.

According to embodiments of the present invention, the first RNA molecule targets a SNP in the promoter, upstream of the promoter, or the UTR of a mutated allele and the second RNA molecule is designed to target a sequence which is present in an intron of both the mutated allele and the functional allele.

According to embodiments of the present invention, the first RNA molecule targets a sequence upstream of the promotor which is present in both a mutated and functional allele and the second RNA molecule targets a SNP or disease-causing mutation in any location of the gene.

According to embodiments of the present invention, there is provided a method comprising removing an exon containing a disease-causing mutation from a mutated allele, wherein the first RNA molecule or the first and the second RNA molecules target regions flanking an entire exon or a portion of the exon.

According to embodiments of the present invention, there is provided a method comprising removing multiple exons, the entire open reading frame of a gene, or removing the entire gene.

According to embodiments of the present invention, the first RNA molecule targets a SNP or disease-causing mutation in an exon or promoter of a mutated allele, and wherein the second RNA molecule targets a SNP in the same or a different exon of the mutated allele, a SNP in an intron, or a sequence in an intron present in both the mutated or functional allele.

According to embodiments of the present invention, the first RNA molecule or the first and the second RNA molecules target an alternative splicing signal sequence between an exon and an intron of a mutant allele.

According to embodiments of the present invention, the second RNA molecule targets a sequence present in both a mutated allele and a functional allele. According to embodiments of the present invention, the second RNA molecule targets an intron.

According to embodiments of the present invention, there is provided a method comprising subjecting the mutant allele to insertion or deletion by an error prone non-homologous end joining (NHEJ) mechanism, generating a frameshift in the mutated allele's sequence.

According to embodiments of the present invention, the frameshift results in inactivation or knockout of the mutated allele.

According to embodiments of the present invention, the frameshift creates an early stop codon in the mutated allele.

According to embodiments of the present invention, the frameshift results in nonsense-mediated mRNA decay of the transcript of the mutant allele.

According to embodiments of the present invention, the inactivating or treating results in a truncated protein encoded by the mutated allele and a functional protein encoded by the functional allele.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-3010 and a CRISPR nuclease inactivating a mutant GUCY2D allele in a cell, comprising delivering to the cell the RNA molecule comprising a guide sequence portion having 17-20 nucleotides in the sequence of 17-20 contiguous nucleotides set forth in any one of SEQ ID NOs: 1-3010 and the CRISPR nuclease.

According to embodiments of the present invention, there is provided a medicament comprising an RNA molecule comprising a guide sequence portion having 17-20 nucleotides in the sequence of 17-20 contiguous nucleotides set forth in any one of SEQ ID NOs: 1-3010 and a CRISPR nuclease for use in inactivating a mutant GUCY2D allele in a cell, wherein the medicament is administered by delivering to the cell the composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided use of a composition comprising an RNA molecule comprising a guide sequence portion having 17-20 nucleotides in the sequence of 17-20 contiguous nucleotides set forth in any one of SEQ ID NOs: 1-3010 and a CRISPR nuclease for treating ameliorating or preventing CORD, comprising delivering to a subject having or at risk of having CORD the composition of comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a medicament comprising the composition comprising an RNA molecule comprising a guide sequence portion having 17-20 nucleotides in the sequence of 17-20 contiguous nucleotides set forth in any one of SEQ ID NOs: 1-3010 and a CRISPR nuclease for use in treating ameliorating or preventing CORD, wherein the medicament is administered by delivering to a subject having or at risk of having CORD: the composition comprising an RNA molecule comprising a guide sequence portion having 17-20 nucleotides in the sequence of 17-20 contiguous nucleotides set forth in any one of SEQ ID NOs: 1-3010 and a CRISPR nuclease.

According to some embodiments of the present invention, there is provided a kit for inactivating a mutant GUCY2D allele in a cell, comprising an RNA molecule comprising a guide sequence portion having 17-20 nucleotides in the sequence of 17-20 contiguous nucleotides set forth in any one of SEQ ID NOs: 1-3010, a CRISPR nuclease, and/or a tracrRNA molecule; and instructions for delivering the RNA molecule; CRISPR nuclease, and/or the tracrRNA to the cell.

According to some embodiments of the present invention, there is provided a kit for treating CORD in a subject, comprising an RNA molecule comprising a guide sequence portion having 17-20 nucleotides in the sequence of 17-20 contiguous nucleotides set forth in any one of SEQ ID NOs: 1-3010, a CRISPR nuclease, and/or a tracrRNA molecule; and instructions for delivering the RNA molecule; CRISPR nuclease, and/or the tracrRNA to a subject having or at risk of having CORD.

In embodiments of the present invention, the RNA molecule comprises a guide sequence portion having 17-20 nucleotides in the sequence of 17-20 contiguous nucleotides set forth in any one of SEQ ID NOs: 1-742, SEQ ID NOs: 743-3010, or SEQ ID NOs 1-3010.

The compositions and methods of the present disclosure may be utilized for treating, preventing, ameliorating, or slowing progression of CORD.

In some embodiments, a mutated allele is deactivated by delivering to a cell an RNA molecule which targets a SNP in the promoter region, the start codon, or the untranslated region (UTR) of the mutated allele.

In some embodiments, a mutated allele is inactivated by removing at least a portion of the promoter and/or removing the start codon and/or a portion of the UTR. In some embodiments, the method of deactivating a mutated allele comprises removing at least a portion of the promoter. In such embodiments one RNA molecule may be designed for targeting a first SNP in the promoter or upstream to the promoter and another RNA molecule is designed to target a second SNP, which is downstream of the first SNP, and is in the promoter, in the UTR, or in an intron or in an exon. Alternatively, one RNA molecule may be designed for targeting a SNP in the promoter, or upstream of the promoter, or the UTR and another RNA molecule is designed to target a sequence which is present in an intron of both the mutated allele and the functional allele. Alternatively, one RNA molecule may be designed for targeting a sequence upstream of the promotor which is present in both the mutated and functional allele and the other guide is designed to target a SNP or disease-causing mutation in any location of the gene e.g., in an exon, intron, UTR, or downstream of the promoter.

In some embodiments, the method of deactivating a mutated allele comprises an exon skipping step comprising removing an exon containing a disease-causing mutation from the mutated allele. Removing an exon containing a disease-causing mutation in the mutated allele requires two RNA molecules which target regions flanking the entire exon or a portion of the exon. Removal of an exon containing the disease-causing mutation may be designed to eliminate the disease-causing action of the protein while allowing for expression of the remaining protein product which retains some or all of the wild-type activity. As an alternative to single exon skipping, multiple exons, the entire open reading frame or the entire gene can be excised using two RNA molecules flanking the region desired to be excised.

In some embodiments, the method of deactivating a mutated allele comprises delivering two RNA molecules to a cell, wherein one RNA molecule targets a SNP or disease-causing mutation in an exon or promoter of the mutated allele, and wherein the other RNA molecule targets a SNP in the same or a different exon of the mutated allele, a SNP in an intron, or a sequence in an intron present in both the mutated or functional allele.

In some embodiments, an RNA molecule is used to target a CRISPR nuclease to an alternative splicing signal sequence between an exon and an intron of a mutant allele, thereby destroying the alternative splicing signal sequence in the mutant allele.

Any one of, or combination of, the above-mentioned strategies for deactivating a mutant allele may be used in the context of the invention.

Additional strategies may be used to deactivate a mutated allele. For example, in embodiments of the present invention, an RNA molecule is used to direct a CRISPR nuclease to an exon or a splice site of a mutated allele in order to create a double-stranded break (DSB), leading to insertion or deletion of nucleotides by an error-prone non-homologous end-joining (NHEJ) mechanism and formation of a frameshift mutation in the mutated allele. The frameshift mutation may result in: (1) inactivation or knockout of the mutated allele by generation of an early stop codon in the mutated allele, resulting in generation of a truncated protein; or (2) nonsense mediated mRNA decay of the transcript of the mutant allele. In further embodiments, one RNA molecule is used to direct a CRISPR nuclease to a promotor of a mutated allele.

In some embodiments, the method of deactivating a mutated allele further comprises enhancing activity of the functional protein such as by providing a protein/peptide, a nucleic acid encoding a protein/peptide, or a small molecule such as a chemical compound, capable of activating/enhancing activity of the functional protein.

According to some embodiments, the present disclosure provides an RNA sequence (RNA molecule') which binds to/associates with and/or directs the RNA guided DNA nuclease e.g., CRISPR nuclease to a sequence comprising at least one nucleotide which differs between a mutated allele and a functional allele (e.g., SNP) of a gene of interest (i.e., a sequence of the mutated allele which is not present in the functional allele).

In some embodiments, the method comprises the steps of: contacting a mutated allele of a gene of interest with an allele-specific RNA molecule and a CRISPR nuclease e.g., a Cas9 protein, wherein the allele-specific RNA molecule and the CRISPR nuclease e.g., Cas9 associate with a nucleotide sequence of the mutated allele of the gene of interest which differs by at least one nucleotide from a nucleotide sequence of a functional allele of the gene of interest, thereby modifying or knocking-out the mutated allele.

In some embodiments, the allele-specific RNA molecule and a CRISPR nuclease is introduced to a cell encoding the gene of interest. In some embodiments, the cell encoding the gene of interest is in a mammalian subject. In some embodiments, the cell encoding the gene of interest is in a plant.

In some embodiments, the cleaved mutated allele is further subjected to insertion or deletion (indel) by an error prone non-homologous end joining (NHEJ) mechanism, generating a frameshift in the mutated allele's sequence. In some embodiments, the generated frameshift results in inactivation or knockout of the mutated allele. In some embodiments, the generated frameshift creates an early stop codon in the mutated allele and results in generation of a truncated protein. In such embodiments, the method results in the generation of a truncated protein encoded by the mutated allele and a functional protein encoded by the functional allele. In some embodiments, a frameshift generated in a mutated allele using the methods of the invention results in nonsense-mediated mRNA decay of the transcript of the mutant allele.

In some embodiments, the mutated allele is an allele of the GUCY2D gene. In some embodiments, the RNA molecule targets a SNP which co-exists with/is genetically linked to the mutated sequence associated with CORD genetic disorder. In some embodiments, the RNA molecule targets a SNP which is highly prevalent in the population and exists in the mutated allele having the mutated sequence associated with CORD genetic disorder and not in the functional allele of an individual subject to be treated. In some embodiments, a disease-causing mutation within a mutated GUCY2D allele is targeted.

In some embodiments, the SNP is within an exon of the gene of interest. In such embodiments, a guide sequence portion of an RNA molecule may be designed to associate with a sequence of the exon of the gene of interest.

In some embodiments, SNP is within an intron or an exon of the gene of interest. In some embodiments, SNP is in close proximity to a splice site between the intron and the exon. In some embodiments, the close proximity to a splice site is 1, 2, 3, 4, 5, 6, 7, 8, 9, 10, 11, 12, 13, 14, 15, 16, 17, 18, 19, or 20 nucleotides upstream or downstream to the splice site. Each possibility represents a separate embodiment of the present invention. In such embodiments, a guide sequence portion of an RNA molecule may be designed to associate with a sequence of the gene of interest which comprises the splice site.

In some embodiments, the method is utilized for treating a subject having a disease phenotype resulting from the heterozygote GUCY2D gene. In such embodiments, the method results in improvement, amelioration or prevention of the disease phenotype.

Embodiments referred to above refer to a CRISPR nuclease, RNA molecule(s), and tracrRNA being effective in a subject or cells at the same time. The CRISPR, RNA molecule(s), and tracrRNA can be delivered substantially at the same time or can be delivered at different times but have effect at the same time. For example, this includes delivering the CRISPR nuclease to the subject or cells before the RNA molecule and/or tracr RNA is substantially extant in the subject or cells.

In some embodiments, the cell is a retinal cell. In some embodiments, the cell is a photoreceptor cell. In some embodiments, the photoreceptor cell is a rod photoreceptor cell. In some embodiments, the photoreceptor cell is a cone photoreceptor cell.

Dominant Genetic Disorders.

One of skill in the art will appreciate that all subjects with any type of heterozygote genetic disorder (e.g., dominant genetic disorder) may be subjected to the methods described herein. In one embodiment, the present invention may be used to target a gene involved in, associated with, or causative of dominant genetic disorders such as, for example CORD. In some embodiments, the dominant genetic disorder is CORD In some embodiments, the target gene is the GUCY2D gene (Entrez Gene, gene ID No: 3000).

CRISPR Nucleases and PAM Recognition

In some embodiments, the sequence specific nuclease is selected from CRISPR nucleases, or a functional variant thereof. In some embodiments, the sequence specific nuclease is an RNA guided DNA nuclease. In such embodiments, the RNA sequence which guides the RNA guided DNA nuclease (e.g., Cpf1) binds to and/or directs the RNA guided DNA nuclease to the sequence comprising at least one nucleotide which differs between a mutated allele and its counterpart functional allele (e.g., SNP). In some embodiments, the CRISPR complex does not further comprise a tracrRNA. In a non-limiting example, in which the RNA guided DNA nuclease is a CRISPR protein, the at least one nucleotide which differs between the dominant mutated allele and the functional allele may be within the PAM site and/or proximal to the PAM site within the region that the RNA molecule is designed to hybridize to. A skilled artisan will appreciate that RNA molecules can be engineered to bind to a target of choice in a genome by commonly known methods in the art.

In embodiments of the present invention, a type II CRISPR system utilizes a mature crRNA:tracrRNA complex directs a CRISPR nuclease, e.g. Cas9, to the target DNA via Watson-Crick base-pairing between the crRNA and the protospacer on the target DNA next to the protospacer adjacent motif (PAM), an additional requirement for target recognition. The CRISPR nuclease then mediates cleavage of target DNA to create a double-stranded break within the protospacer. A skilled artisan will appreciate that each of the engineered RNA molecule of the present invention is further designed such as to associate with a target genomic DNA sequence of interest next to a protospacer adjacent motif (PAM), e.g., a PAM matching the sequence relevant for the type of CRISPR nuclease utilized, such as for a non-limiting example, NGG or NAG, wherein "N" is any nucleobase, for Streptococcus pyogenes Cas9 WT (SpCAS9); NNGRRT for Staphylococcus aureus (SaCas9); NNNVRYM for Jejuni Cas9 WT; NGAN or NGNG for SpCas9-VQR variant; NGCG for SpCas9-VRER variant; NGAG for SpCas9-EQR variant; NNNNGATT for *Neisseria meningitidis* (NmCas9); or TTTV for Cpf1. RNA molecules of the present invention are each designed to form complexes in conjunction with one or more different CRISPR nucleases and designed to target polynucleotide sequences of interest utilizing one or more different PAM sequences respective to the CRISPR nuclease utilized.

In some embodiments, an RNA-guided DNA nuclease e.g., a CRISPR nuclease, may be used to cause a DNA break at a desired location in the genome of a cell. The most commonly used RNA-guided DNA nucleases are derived from CRISPR systems, however, other RNA-guided DNA nucleases are also contemplated for use in the genome editing compositions and methods described herein. For instance, see U.S. Patent Publication No. 2015-0211023, incorporated herein by reference.

CRISPR systems that may be used in the practice of the invention vary greatly. CRISPR systems can be a type I, a type II, or a type III system. Non-limiting examples of suitable CRISPR proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas1 Od, CasF, CasG, CasH, Csy1 , Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3,Csx17, Csx14, Csx10, Csx16, CsaX, Csx3, Csz1, Csx15, Csf1, Csf2, Csf3, Csf4, and Cul966.

In some embodiments, the RNA-guided DNA nuclease is a CRISPR nuclease derived from a type II CRISPR system (e.g., Cas9). The CRISPR nuclease may be derived from *Streptococcus pyogenes, Streptococcus thermophilus, Streptococcus* sp., *Staphylococcus aureus, Neisseria meningitidis, Treponema denticola, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculumthermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus, Acaryochloris marina*, or any species which encodes a CRISPR nuclease with a known PAM sequence. CRISPR nucleases encoded by uncultured bacteria may also be used in the context of the invention. (See Burstein et al. Nature, 2017). Variants of CRIPSR proteins having known PAM sequences e.g., spCas9 D1135E variant, spCas9 VQR variant, spCas9 EQR variant, or spCas9 VRER variant may also be used in the context of the invention.

Thus, an RNA guided DNA nuclease of a CRISPR system, such as a Cas9 protein or modified Cas9 or homolog or ortholog of Cas9, or other RNA guided DNA nucleases belonging to other types of CRISPR systems, such as Cpf1 and its homologs and orthologs, may be used in the compositions of the present invention.

In certain embodiments, the CRIPSR nuclease may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein.

In some embodiments, the CRISPR nuclease is Cpf1. Cpf1 is a single RNA-guided endonuclease which utilizes a T-rich protospacer-adjacent motif. Cpf1 cleaves DNA via a staggered DNA double-stranded break. Two Cpf1 enzymes from Acidaminococcus and Lachnospiraceae have been shown to carry out efficient genome-editing activity in human cells. (See Zetsche et al. (2015) Cell.).

Thus, an RNA guided DNA nuclease of a Type II CRISPR System, such as a Cas9 protein or modified Cas9 or homologs, orthologues, or variants of Cas9, or other RNA guided DNA nucleases belonging to other types of CRISPR systems, such as Cpf1 and its homologs, orthologues, or variants, may be used in the present invention.

In some embodiments, the guide molecule comprises one or more chemical modifications which imparts a new or improved property (e.g., improved stability from degradation, improved hybridization energetics, or improved binding properties with an RNA guided DNA nuclease). Suitable chemical modifications include, but are not limited to: modified bases, modified sugar moieties, or modified internucleoside linkages. Non-limiting examples of suitable chemical modifications include: 4-acetylcytidine, 5-(carboxyhydroxymethyl)uridine, 2'-O-methylcytidine, 5-carboxymethylaminomethyl-2-thiouridine, 5-carboxymethylaminomethyluridine, dihydrouridine, 2'-O-methylpseudouridine, "beta, D-galactosylqueuosine", 2'-O-methylguanosine, inosine, N6-isopentenyl adenosine, 1-methyladenosine, 1-methylpseudouridine, 1-methylguanosine, 1-methylinosine, "2,2-dimethylguanosine", 2-methyladenosine, 2-methylguanosine, 3-methylcytidine, 5-methylcytidine, N6-methyladenosine, 7-methylguanosine, 5-methylaminomethyluridine, methoxyaminomethyl-2-thiouridine, "beta, D-mannosylqueuosine", methoxycarbonylmethyl-2-thiouridine, 5-methoxycarbonylmethyluridine, 5-methoxyudridine, 2-methylthio-N6-isopentenyladenosine, N-((9-beta-D-ribofuranosyl-2-methylthiopurine-6-yl) carbamoyl)threonine, N-((9-beta-D-ribofuranosylpurine-6-yl)N-methylcarbamoyl)threonine, uridine-5-oxyacetic acid-methylester, uridine-5-oxyacetic acid, wybutoxosine, queuosine, 2-thiocytidine, 5-methyl-2-thiourdine, 2-thiouridine, 4-thiouridine, 5-methyluridine, N-((9-beta-D-ribofuranosylpurine-6-yl)-carbamoyl)threonine, 2'-O-methyl-5-methyluridine, 2'-O-methyluridine, wybutosine, "3-(3-amino-3-carboxy-propyl)uridine, (acp3)u", 2'-0-methyl (M), 3'-phosphorothioate (MS), 3'-thioPACE (MSP), pseudouridine, or 1-methyl pseudo-uridine. Each possibility represents a separate embodiment of the present invention.

Guide Sequences which Specifically Target a Mutant Allele

A given gene may contain thousands of SNPs. Utilizing a 24 base pair target window for targeting each SNP in a gene would require hundreds of thousands of guide sequences. Any given guide sequence when utilized to target a SNP may result in degradation of the guide sequence, limited activity, no activity, or off-target effects. Accordingly, suitable guide sequences are necessary for targeting a given gene. By the present invention, a novel set of guide sequences have been identified for knocking out expression of a mutated GUCY2D protein, inactivating a mutant GUCY2D gene allele, and treating CORD.

The present disclosure provides guide sequences capable of specifically targeting a mutated allele for inactivation while leaving the functional allele unmodified. The guide sequences of the present invention are designed to, and are most likely to, specifically differentiate between a mutated allele and a functional allele. Of all possible guide sequences which target a mutated allele desired to be inactivated, the specific guide sequences disclosed herein are specifically effective to function with the disclosed embodiments.

Briefly, the guide sequences may have properties as follows: (1) target SNP/insertion/deletion/indel with a high prevalence in the general population, in a specific ethnic population or in a patient population is above 1% and the SNP/insertion/deletion/indel heterozygosity rate in the same population is above 1%; (2) target a location of a SNP/insertion/deletion/indel proximal to a portion of the gene e.g., within 5 k bases of any portion of the gene, for example, a promoter, a UTR, an exon or an intron; and (3) target a mutant allele using an RNA molecule which targets a founder or common pathogenic mutations for the disease/gene. In some embodiments, the prevalence of the SNP/insertion/deletion/indel in the general population, in a specific ethnic population or in a patient population is above 1%, 2%, 3%, 4%, 5%, 6%, 7%, 8%, 9%, 10%, 11%, 12%, 13%, 14%, or 15% and the SNP/insertion/deletion/indel heterozygosity rate in the same population is above 1%, 2%, 3%, 4%, 5%, 6%, 7%, 8%, 9%, 10%, 11%, 12%, 13%, 14%, or 15%. Each possibility represents a separate embodiment and may be combined at will.

For each gene, according to SNP/insertion/deletion/indel any one of the following strategies may be used to deactivate the mutated allele: (1) Knockout strategy using one RNA molecule—one RNA molecule is utilized to direct a CRISPR nuclease to a mutated allele and create a double-strand break (DSB) leading to formation of a frameshift mutation in an exon or in a splice site region of the mutated allele; (2) Knockout strategy using two RNA molecules—two RNA molecules are utilized. A first RNA molecule targets a region in the promoter or an upstream region of a mutated allele and another RNA molecule targets downstream of the first RNA molecule in a promoter, exon, or intron of the mutated allele; (3) Exon(s) skipping strategy—one RNA molecule may be used to target a CRISPR nuclease to a splice site region, either at the 5' end of an intron (donor sequence) or the 3' end of an intron (acceptor sequence), in order to destroy the splice site. Alternatively, two RNA molecules may be utilized such that a first RNA molecule targets an upstream region of an exon and a second RNA molecule targets a region downstream of the first RNA molecule, thereby excising the exon(s). Based on the locations of identified SNPs/insertions/deletions/indels for each mutant allele, any one of, or a combination of, the above-mentioned methods to deactivate the mutant allele may be utilized.

When only one RNA molecule is used is that the location of the SNP is in an exon or in close proximity (e.g., within 20 basepairs) to a splice site between the intron and the exon. When two RNA molecules are used, guide sequences may target two SNPs such that the first SNP is upstream of exon 1 e.g., within the 5' untranslated region, or within the promoter or within the first 2 kilobases 5' of the transcription start site, and the second SNP is downstream of the first SNP e.g., within the first 2 kilobases 5' of the transcription start site, or within intron 1, 2 or 3, or within exon 1, exon 2, or exon 3.

Guide sequences of the present invention may target a SNP in the upstream portion of the targeted gene, preferably upstream of the last exon of the targeted gene. Guide sequences may target a SNP upstream to exon 1, for example within the 5' untranslated region, or within the promoter or within the first 4-5 kilobases 5' of the transcription start site.

Guide sequences of the present invention may also target a SNP within close proximity (e.g., within 50 basepairs, more preferably with 20 basepairs) to a known protospacer adjacent motif (PAM) site.

Guide sequences of the present invention also may target: (1) a heterozygous SNP for the targeted gene; (2) a heterozygous SNPs upstream and downstream of the gene; (3) a SNPs with a prevalence of the SNP/insertion/deletion/indel in the general population, in a specific ethnic population, or in a patient population above 1%; (4) have a guanine-cytosine content of greater than 30% and less than 85%; (5) have no repeat of 4 or more thymine/uracil or 8 or more guanine, cytosine, or adenine; (6) having no off-target identified by off-target analysis; and (7) preferably target Exons over Introns or be upstream of a SNP rather than downstream of a SNP.

In embodiments of the present invention, the SNP may be upstream or downstream of the gene. In embodiments of the present invention, the SNP is within 4,000 base pairs upstream or downstream of the gene.

The at least one nucleotide which differs between the mutated allele and the functional allele, may be upstream, downstream or within the sequence of the disease-causing mutation of the gene of interest. The at least one nucleotide which differs between the mutated allele and the functional allele, may be within an exon or within an intron of the gene of interest. In some embodiments, the at least one nucleotide which differs between the mutated allele and the functional allele is within an exon of the gene of interest. In some embodiments, the at least one nucleotide which differs between the mutated allele and the functional allele is within an intron or an exon of the gene of interest, in close proximity to a splice site between the intron and the exon e.g., 1, 2, 3, 4, 5, 6, 7, 8, 9, 10, 11, 12, 13, 14, 15, 16, 17, 18, 19, or 20 nucleotides upstream or downstream to the splice site.

In some embodiments, the at least one nucleotide is a single nucleotide polymorphisms (SNPs). In some embodiments, each of the nucleotide variants of the SNP may be expressed in the mutated allele. In some embodiments, the SNP may be a founder or common pathogenic mutation. Guide sequences may target a SNP which has both (1) a high prevalence in the general population e.g., above 1% in the population; and (2) a high heterozygosity rate in the population, e.g., above 1%. Guide sequences may target a SNP that is globally distributed. A SNP may be a founder or common pathogenic mutation. In some embodiments, the prevalence in the general population is above 1%, 2%, 3%, 4%, 5%, 6%, 7%, 8%, 9%, 10%, 11%, 12%, 13%, 14%, or 15%. Each possibility represents a separate embodiment. In some embodiments, the heterozygosity rate in the population is above 1%, 2%, 3%, 4%, 5%, 6%, 7%, 8%, 9%, 10%, 11%, 12%, 13%, 14%, or 15%. Each possibility represents a separate embodiment.

In some embodiments, the at least one nucleotide which differs between the mutated allele and the functional allele is linked to/co-exists with the disease-causing mutation in high prevalence in a population. In such embodiments, "high prevalence" refers to at least 92%, 93%, 94%, 95%, 96%, 97%, 98%, 99%, or 100%. Each possibility represents a separate embodiment of the present invention. In one embodiment, the at least one nucleotide which differs between the mutated allele and the functional allele, is a disease-associated mutation. In some embodiments, the SNP is highly prevalent in the population. In such embodiments, "highly prevalent" refers to at least 10%, 11%, 12%, 13%, 14%, 15%, 20%, 30%, 40%, 50%, 60%, or 70% of a population. Each possibility represents a separate embodiment of the present invention.

Guide sequences of the present invention may satisfy any one of the above criteria and are most likely to differentiate between a mutated allele from its corresponding functional allele.

In some embodiments the RNA molecule targets a SNP/WT sequence linked to SNPs as shown in Table 1 below. The SNP details are indicated in the 1$^{st}$ column and include: SNP ID No. (based on NCBI's 2018 database of Single Nucleotide Polymorphisms (dbSNP)). For variants with no available rs number variants characteristic are indicated based on gnomAD 2018 browser database. The 2$^{nd}$ column indicates an assigned identifier for each SNP. The 3$^{rd}$ column indicates the location of each SNP on the GUCY2D gene.

TABLE 1

GUCY2D gene SNPs

| RSID | SNP No. | SNP location in the gene |
| --- | --- | --- |
| rs761913009 | s1 | Intron_19 of 19 |
| 17:7923438_C_T | s2 | Intron_19 of 19 |
| 17:7923435_C_T | s3 | Intron_19 of 19 |
| 17:7923434_G_T | s4 | Intron_19 of 19 |
| rs56300556 | s5 | downstream +1113 bp |
| rs867805871 | s6 | downstream +1112 bp |
| rs760500680 | s7 | downstream +1106 bp |
| rs3813585 | s8 | Intron_14 of 19 |
| rs7503918 | s9 | Intron_19 of 19 |
| rs4791456 | s10 | downstream +203 bp |
| rs9889612 | s11 | upstream −1603 bp |
| rs11655487 | s12 | Intron_12 of 19 |
| rs7501868 | s13 | Intron_19 of 19 |
| rs4792111 | s14 | Intron_19 of 19 |
| rs7501530 | s15 | upstream −2377 bp |
| rs61749665 | s16 | Exon_2 of 20 |
| rs12103521 | s17 | Intron_19 of 19 |
| rs2816 | s18 | Exon_20 of 20 |
| rs8069344 | s19 | Exon_12 of 20 |
| rs12103519 | s20 | Intron_19 of 19 |
| rs8071166 | s21 | Intron_19 of 19 |
| rs72841478 | s22 | Intron_3 of 19 |
| rs11655691 | s23 | Intron_19 of 19 |
| rs56130505 | s24 | Exon_10 of 20 |
| rs3829789 | s25 | Exon_3 of 20 |
| rs34922798 | s26 | Intron_8 of 19 |
| rs9905402 | s27 | Exon_2 of 20 |
| rs72841482 | s28 | Intron_13 of 19 |
| rs8068722 | s29 | Intron_13 of 19 |
| rs73237655 | s30 | Intron_7 of 19 |
| rs9914686 | s31 | Intron_3 of 19 |
| rs12449814 | s32 | Intron_7 of 19 |
| rs73237639 | s33 | upstream −3180 bp |
| rs9903069 | s34 | upstream −2486 bp |
| 17:7906016_C_T | s35 | Exon_1 of 20 |
| rs34598902 | s36 | Exon_10 of 20 |
| rs57490393 | s37 | downstream +1088 bp |
| rs57307096 | s38 | downstream +1090 bp |
| rs12103471 | s39 | Intron_13 of 19 |
| rs80076597 | s40 | Intron_19 of 19 |
| rs56348143 | s41 | Intron_16 of 19 |
| rs60130989 | s42 | Intron_10 of 19 |
| rs57477973 | s43 | downstream +2441 bp |
| rs58765638 | s44 | downstream +2669 bp |
| rs112984002 | s45 | Intron_5 of 19 |
| rs73978653 | s46 | Intron_7 of 19 |
| rs142351773 | s47 | Exon_19 of 20 |
| rs116870332 | s48 | Intron_16 of 19 |
| rs138596240 | s49 | Exon_20 of 20 |
| rs56034424 | s50 | Exon_4 of 20 |
| rs139731548 | s51 | Intron_9 of 19 |
| rs79887212 | s52 | Intron_18 of 19 |
| rs74656480 | s53 | Intron_19 of 19 |
| rs78901930 | s54 | Exon_20 of 20 |
| rs73978656 | s55 | Intron_19 of 19 |
| rs73978658 | s56 | Intron_19 of 19 |
| rs73978654 | s57 | Intron_19 of 19 |
| rs4791452 | s58 | Intron_7 of 19 |
| rs57184071 | s59 | Intron_8 of 19 |
| rs72841481 | s60 | Intron_11 of 19 |
| rs80245692 | s61 | Intron_5 of 19 |
| rs28743021 | s62 | Exon_8 of 20 |
| rs78844078 | s63 | Intron_16 of 19 |
| rs78380494 | s64 | Intron_19 of 19 |
| rs56316238 | s65 | Exon_13 of 20 |
| rs73978655 | s66 | Intron_19 of 19 |
| rs2534 | s67 | Intron_8 of 19 |
| rs75290069 | s68 | Intron_3 of 19 |
| rs34594470 | s69 | Intron_8 of 19 |
| rs9891219 | s70 | Intron_8 of 19 |
| rs6503069 | s71 | downstream +1197 bp |
| rs34898068 | s72 | upstream −2657 bp |
| rs67594392 | s73 | Intron_19 of 19 |
| rs9901134 | s74 | upstream −3866 bp |
| rs79016382 | s75 | downstream +3155 bp |
| rs149260011 | s76 | Intron_8 of 19 |

Delivery to Cells

The RNA molecule compositions described herein may be delivered to a target cell by any suitable means. RNA molecule compositions of the present invention may be targeted to any cell which contains and/or expresses a dominant negative allele, including any mammalian or plant cell. For example, in one embodiment the RNA molecule specifically targets a mutated GUCY2D allele and the target cell is a retinal cell such as pigment epithelium (RPE), photoreceptors (e.g., rod and cone), glial cells (e.g., Müller), and ganglion cells. Further, the nucleic acid compositions described herein may be delivered as one or more DNA molecules, RNA molecules, Ribonucleoproteins (RNP), nucleic acid vectors, or any combination thereof.

In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thio-PACE (MSP), pseudouridine, and 1-methyl pseudo-uridine. Each possibility represents a separate embodiment of the present invention.

Any suitable viral vector system may be used to deliver nucleic acid compositions e.g., the RNA molecule compositions of the subject invention. Conventional viral and non-viral based gene transfer methods can be used to introduce nucleic acids and target tissues. In certain embodiments, nucleic acids are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson (1992) Science 256:808-813; Nabel & Felgner (1993) TIBTECH 11:211-217; Mitani & Caskey (1993) TIBTECH 11:162-166; Dillon (1993) TIBTECH 11:167-175; Miller (1992) Nature 357:455-460; Van Brunt (1988) Biotechnology 6(10):1149-1154; Vigne (1995) Restorative Neurology and Neuroscience 8:35-36; Kremer & Perricaudet (1995) British Medical Bulletin 51(1):31-44; Haddada et al. (1995) in Current Topics in Microbiology and Immunology Doerfler and Bohm (eds.); and Yu et al. (1994) Gene Therapy 1:13-26.

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid:nucleic acid conjugates, artificial virions, and agent-enhanced uptake of nucleic acids or can be delivered to plant cells by bacteria or viruses (e.g., *Agrobacterium, Rhizobium* sp. NGR234, Sinorhizoboiummeliloti, Mesorhizobium loti, tobacco mosaic virus, potato virus X, cauliflower mosaic virus and cassava vein mosaic virus). (See, e.g., Chung et al. (2006) Trends Plant Sci. 11(1):1-4). Sonoporation using, e.g., the Sonitron 2000 system (Rich-Mar), can also be used for delivery of nucleic acids. Cationic-lipid mediated delivery of proteins and/or nucleic acids is also contemplated as an in vivo or in vitro delivery method. (See Zuris et al. (2015) Nat. Biotechnol. 33(1):73-80; see also Coelho et al. (2013) N. Engl. J. Med. 369, 819-829; Judge et al. (2006) Mol. Ther. 13, 494-505; and Basha et al. (2011) Mol. Ther. 19, 2186-2200).

Additional exemplary nucleic acid delivery systems include those provided by Amaxa.RTM. Biosystems (Cologne, Germany), Maxcyte, Inc. (Rockville, Md.), BTX Molecular Delivery Systems (Holliston, Mass.) and Copernicus Therapeutics Inc., (see, e.g., U.S. Pat. No. 6,008,336). Lipofection is described in e.g., U.S. Pat. No. 5,049,386, U.S. Pat. No. 4,946,787; and U.S. Pat. No. 4,897,355, and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (See, e.g., Crystal (1995) Science 270:404-410; Blaese et al. (1995) Cancer Gene Ther. 2:291-297; Behr et al. (1994) Bioconjugate Chem. 5:382-389; Remy et al. (1994) Bioconjugate Chem. 5:647-654; Gao et al. (1995) Gene Therapy 2:710-722; Ahmad et al. (1992) Cancer Res. 52:4817-4820; U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al (2009) Nature Biotechnology 27(7):643).

The use of RNA or DNA viral based systems for viral mediated delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, retroviral, lentivirus, adenoviral, adeno-associated, vaccinia and herpes simplex virus vectors for gene transfer.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (See, e.g., Buchschacher et al. (1992) J. Virol. 66:2731-2739; Johann et al. (1992) J. Virol. 66:1635-1640; Sommerfelt et al. (1990) Virol. 176:58-59; Wilson et al. (1989) J. Virol. 63:2374-2378; Miller et al. (1991) J. Virol. 65:2220-2224; PCT/US94/05700).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) Blood 85:3048-305; Kohn et al.(1995) Nat. Med. 1:1017-102; Malech et al. (1997) PNAS 94:22 12133-12138). PA317/pLASN was the first therapeutic vector used in a gene therapy trial. (Blaese et al. (1995). Transduction efficiencies of 50% or greater have been observed for MFG-S packaged vectors. (Ellem et al. (1997) Immunol Immunother. 44(1):10-20; Dranoff et al. (1997) Hum. Gene Ther. 1:111-2).

Packaging cells are used to form virus particles that are capable of infecting a host cell. Such cells include 293 cells, which package adenovirus, AAV, and Psi-2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) Proc. Natl. Acad. Sci. USA 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravitreal, intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid composition, and re-infused back into the subject organism (e.g., patient). Various cell types suitable for ex vivo transfection are well known to those of skill in the art (See, e.g., Freshney et al. (1994) Culture of Animal Cells, A Manual of Basic Technique, 3rd ed, and the references cited therein for a discussion of how to isolate and culture cells from patients).

Suitable cells include, but are not limited to, eukaryotic cells and/or cell lines. Non-limiting examples of such cells or cell lines generated from such cells include COS, CHO (e.g., CHO—S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), perC6 cells, any plant cell (differentiated or undifferentiated), as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with a guided nuclease system (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-gamma, and TNF-alpha are known (as a non-limiting example see, Inaba et al., J. Exp. Med. 176:1693-1702 (1992)). Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (as a non-limiting example see Inaba et al. (1992) J. Exp. Med. 176:1693-1702). Stem cells that have been modified may also be used in some embodiments.

Any one of the RNA molecule compositions described herein is suitable for genome editing in post-mitotic cells or any cell which is not actively dividing, e.g., arrested cells. Examples of post-mitotic cells which may be edited using a composition of the present invention include, but are not limited to, a photoreceptor cell, a rod photoreceptor cell, a cone photoreceptor cell, a retinal pigment epithelium (RPE), a glial cell, Muller cell, and a ganglion.

Vectors (e.g., retroviruses, liposomes, etc.) containing therapeutic nucleic acid compositions can also be administered directly to an organism for transduction of cells in vivo. Administration is by any of the routes normally used for introducing a molecule into ultimate contact with blood or tissue cells including, but not limited to, injection, infusion, topical application (e.g., eye drops and cream) and electroporation. Suitable methods of administering such nucleic acids are available and well known to those of skill in the art, and, although more than one route can be used to administer a particular composition, a particular route can often provide a more immediate and more effective reaction than another route. According to some embodiments, the composition is delivered via sub-retinal injection. According to some embodiments, the composition is delivered via intravitreal injection.

Vectors suitable for introduction of transgenes into immune cells (e.g., T-cells) include non-integrating lentivirus vectors. See, e.g., U.S. Patent Publication No. 2009-0117617.

Pharmaceutically acceptable carriers are determined in part by the particular composition being administered, as well as by the particular method used to administer the composition. Accordingly, there is a wide variety of suitable formulations of pharmaceutical compositions available, as described below (See, e.g., Remington's Pharmaceutical Sciences, 17th ed., 1989).

In accordance with some embodiments, there is provided an RNA molecule which binds to associates with and/or directs the RNA guided DNA nuclease to a sequence comprising at least one nucleotide which differs between a mutated allele and a functional allele (e.g., SNP) of a gene of interest (i.e., a sequence of the mutated allele which is not present in the functional allele). The sequence may be within the disease associated mutation. The sequence may be upstream or downstream to the disease associated mutation. Any sequence difference between the mutated allele and the functional allele may be targeted by an RNA molecule of the present invention to inactivate the mutant allele, or otherwise disable its dominant disease-causing effects, while preserving the activity of the functional allele.

The disclosed compositions and methods may also be used in the manufacture of a medicament for treating dominant genetic disorders in a patient.

Examples of RNA Guide Sequences which Specifically Target Mutated Alleles of GUCY2D Gene Although a large number of guide sequences can be designed to target a mutated allele, the nucleotide sequences described in Tables 2 identified by SEQ ID NOs: 1-3010 below were specifically selected to effectively implement the methods set forth herein and to effectively discriminate between alleles.

Referring to columns 1-4, each of SEQ ID NOs. 1-3010 indicated in column 1 corresponds to an engineered guide sequence. The corresponding SNP details are indicated in column 2. The SNP details indicated in the 2nd column include the assigned identifier for each SNP corresponding to a SNP ID indicated in Table 1. Column 3 indicates whether the target of each guide sequence is the GUCY2D gene polymorph or wild type (REF) sequence. Column 4 indicates the guanine-cytosine content of each guide sequence.

Table 2 shows guide sequences designed for use as described in the embodiments above to associate with different SNPs within a sequence of a mutated GUCY2D allele. Each engineered guide molecule is further designed such as to associate with a target genomic DNA sequence of interest that lies next to a protospacer adjacent motif (PAM), e.g., a PAM matching the sequence NGG or NAG, where "N" is any nucleobase. The guide sequences were designed to work in conjunction with one or more different CRISPR nucleases, including, but not limited to, e.g. SpCas9WT (PAM SEQ: NGG), SpCas9.VQR.1 (PAM SEQ: NGAN), SpCas9.VQR.2 (PAM SEQ: NGNG), SpCas9.EQR (PAM SEQ: NGAG), SpCas9.VRER (PAM SEQ: NGCG), SaCas9WT (PAM SEQ: NNGRRT), NmCas9WT (PAM SEQ: NNNNGATT), Cpf1(PAM SEQ: TTTV), or JeCas9WT (PAM SEQ: NNNVRYM). RNA molecules of the present invention are each designed to form complexes in conjunction with one or more different CRISPR nucleases and designed to target polynucleotide sequences of interest utilizing one or more different PAM sequences respective to the CRISPR nuclease utilized

TABLE 2

Guide sequences designed to associate with specific SNPs of the GUCY2D gene

| SEQ ID NO: | SNP ID (Table 1) | Target (SNP/REF) | % GC |
|---|---|---|---|
| 1 | s1, s2, s3, s4 | REF, REF, REF, REF | 50% |
| 2 | s1, s2, s3, s4 | REF, REF, REF, REF | 50% |
| 3 | s1, s2, s3, s4 | REF, REF, REF, REF | 45% |
| 4 | s8 | BOTH | 40% |
| 5 | s8 | BOTH | 45% |
| 6 | s8 | BOTH | 40% |
| 7 | s9 | BOTH | 50% |
| 8 | s9 | BOTH | 55% |
| 9 | s9 | BOTH | 55% |
| 10 | s9 | BOTH | 45% |
| 11 | s11 | BOTH | 45% |
| 12 | s11 | BOTH | 45% |
| 13 | s12 | BOTH | 60% |
| 14 | s12 | BOTH | 50% |
| 15 | s15 | BOTH | 35% |
| 16 | s16 | BOTH | 65% |
| 17 | s16 | BOTH | 70% |
| 18 | s17 | BOTH | 65% |
| 19 | s17 | BOTH | 65% |
| 20 | s18 | BOTH | 60% |
| 21 | s20 | BOTH | 70% |
| 22 | s20 | BOTH | 70% |
| 23 | s21 | BOTH | 50% |
| 24 | s21 | BOTH | 65% |
| 25 | s21 | BOTH | 45% |
| 26 | s22 | BOTH | 45% |
| 27 | s22 | BOTH | 45% |
| 28 | s23 | BOTH | 60% |
| 29 | s23 | BOTH | 70% |
| 30 | s25 | BOTH | 75% |
| 31 | s25 | BOTH | 70% |
| 32 | s25 | BOTH | 70% |
| 33 | s27 | BOTH | 85% |
| 34 | s27 | BOTH | 85% |
| 35 | s27 | BOTH | 80% |
| 36 | s31 | BOTH | 55% |
| 37 | s32 | BOTH | 60% |
| 38 | s32 | BOTH | 70% |
| 39 | s33 | BOTH | 35% |
| 40 | s33 | BOTH | 40% |
| 41 | s34 | BOTH | 45% |
| 42 | s35 | BOTH | 90% |
| 43 | s35 | BOTH | 90% |
| 44 | s35 | BOTH | 80% |
| 45 | s36, s24 | REF, BOTH | 70% |
| 46 | s36, s24 | REF, BOTH | 70% |
| 47 | s36, s24 | REF, BOTH | 70% |
| 48 | s36, s24 | REF, REF | 75% |
| 49 | s36, s24 | REF, REF | 70% |
| 50 | s36, s24 | REF, REF | 75% |
| 51 | s36, s24 | REF, REF | 75% |
| 52 | s36, s24 | REF, REF | 75% |
| 53 | s36, s24 | REF, REF | 65% |
| 54 | s36, s24 | REF, REF | 70% |
| 55 | s36, s24 | REF, REF | 70% |
| 56 | s36, s24 | REF, REF | 70% |
| 57 | s36, s24 | REF, REF | 75% |
| 58 | s36, s24 | BOTH, REF | 60% |
| 59 | s36, s24 | BOTH, REF | 60% |
| 60 | s36, s24 | BOTH, REF | 65% |
| 61 | s29, s39 | REF, BOTH | 65% |
| 62 | s29, s39 | REF, REF | 70% |
| 63 | s29, s39 | REF, REF | 70% |
| 64 | s41 | BOTH | 55% |
| 65 | s41 | BOTH | 75% |
| 66 | s41 | BOTH | 60% |
| 67 | s42 | BOTH | 80% |
| 68 | s42 | BOTH | 60% |
| 69 | s42 | BOTH | 80% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 70 | s42 | BOTH | 75% |
| 71 | s2, s3, s4 | REF, BOTH, BOTH | 65% |
| 72 | s2, s3, s4 | REF, BOTH, BOTH | 65% |
| 73 | s2 | BOTH | 65% |
| 74 | s2 | BOTH | 70% |
| 75 | s45 | BOTH | 45% |
| 76 | s46 | BOTH | 60% |
| 77 | s46 | BOTH | 65% |
| 78 | s46 | BOTH | 55% |
| 79 | s47 | BOTH | 70% |
| 80 | s47 | BOTH | 50% |
| 81 | s47 | BOTH | 70% |
| 82 | s47 | BOTH | 70% |
| 83 | s47 | BOTH | 45% |
| 84 | s48 | BOTH | 65% |
| 85 | s49 | BOTH | 60% |
| 86 | s50 | BOTH | 70% |
| 87 | s50 | BOTH | 75% |
| 88 | s52 | BOTH | 65% |
| 89 | s52 | BOTH | 60% |
| 90 | s53 | BOTH | 50% |
| 91 | s53 | BOTH | 45% |
| 92 | s54 | BOTH | 55% |
| 93 | s54 | BOTH | 55% |
| 94 | s54 | BOTH | 55% |
| 95 | s55 | BOTH | 45% |
| 96 | s55 | BOTH | 50% |
| 97 | s56 | BOTH | 55% |
| 98 | s56 | BOTH | 65% |
| 99 | s56 | BOTH | 50% |
| 100 | s56 | BOTH | 65% |
| 101 | s57 | BOTH | 65% |
| 102 | s57 | BOTH | 45% |
| 103 | s58 | BOTH | 45% |
| 104 | s58 | BOTH | 40% |
| 105 | s59 | BOTH | 50% |
| 106 | s61 | BOTH | 55% |
| 107 | s61 | BOTH | 50% |
| 108 | s62 | BOTH | 55% |
| 109 | s62 | BOTH | 60% |
| 110 | s62 | BOTH | 50% |
| 111 | s63, s48 | REF, BOTH | 70% |
| 112 | s63, s48 | BOTH, REF | 65% |
| 113 | s63, s48 | REF, REF | 70% |
| 114 | s63, s48 | REF, REF | 60% |
| 115 | s63, s48 | REF, REF | 65% |
| 116 | s63, s48 | REF, REF | 70% |
| 117 | s63, s48 | REF, REF | 60% |
| 118 | s63, s48 | REF, REF | 70% |
| 119 | s63, s48 | REF, REF | 65% |
| 120 | s63, s48 | REF, REF | 55% |
| 121 | s63, s48 | REF, REF | 65% |
| 122 | s63, s48 | REF, REF | 55% |
| 123 | s63 | BOTH | 75% |
| 124 | s64, s17 | BOTH, REF | 45% |
| 125 | s64, s17 | REF, REF | 40% |
| 126 | s64, s17 | REF, REF | 45% |
| 127 | s64, s17 | REF, REF | 40% |
| 128 | s64, s17 | REF, REF | 40% |
| 129 | s64 | BOTH | 70% |
| 130 | s65 | BOTH | 65% |
| 131 | s65 | BOTH | 65% |
| 132 | s66 | BOTH | 65% |
| 133 | s67 | BOTH | 55% |
| 134 | s67 | BOTH | 40% |
| 135 | s67 | BOTH | 35% |
| 136 | s68 | BOTH | 35% |
| 137 | s68 | BOTH | 40% |
| 138 | s1 | SNP | 45% |
| 139 | s8 | REF | 45% |
| 140 | s8 | SNP | 50% |
| 141 | s8 | REF | 50% |
| 142 | s8 | SNP | 55% |
| 143 | s8 | SNP | 55% |
| 144 | s8 | REF | 40% |
| 145 | s8 | SNP | 45% |
| 146 | s8 | SNP | 65% |
| 147 | s8 | REF | 55% |
| 148 | s8 | SNP | 60% |
| 149 | s8 | REF | 40% |
| 150 | s8 | REF | 45% |
| 151 | s8 | SNP | 50% |
| 152 | s8 | SNP | 45% |
| 153 | s8 | REF | 40% |
| 154 | s9 | REF | 65% |
| 155 | s9 | SNP | 60% |
| 156 | s9 | REF | 60% |
| 157 | s9 | SNP | 55% |
| 158 | s9 | SNP | 60% |
| 159 | s9 | REF | 65% |
| 160 | s9 | REF | 70% |
| 161 | s9 | SNP | 65% |
| 162 | s9 | SNP | 60% |
| 163 | s9 | REF | 65% |
| 164 | s9 | SNP | 60% |
| 165 | s9 | REF | 65% |
| 166 | s9 | REF | 60% |
| 167 | s9 | SNP | 55% |
| 168 | s9 | REF | 65% |
| 169 | s9 | SNP | 60% |
| 170 | s9 | SNP | 60% |
| 171 | s9 | REF | 65% |
| 172 | s9 | SNP | 55% |
| 173 | s9 | REF | 60% |
| 174 | s9 | SNP | 55% |
| 175 | s9 | REF | 60% |
| 176 | s9 | SNP | 55% |
| 177 | s9 | REF | 60% |
| 178 | s9 | SNP | 55% |
| 179 | s9 | REF | 60% |
| 180 | s9 | SNP | 50% |
| 181 | s9 | REF | 55% |
| 182 | s70 | REF | 60% |
| 183 | s70 | SNP | 60% |
| 184 | s70 | SNP | 70% |
| 185 | s70 | SNP | 55% |
| 186 | s11 | SNP | 40% |
| 187 | s11 | REF | 35% |
| 188 | s11 | SNP | 50% |
| 189 | s11 | REF | 45% |
| 190 | s11 | REF | 40% |
| 191 | s11 | SNP | 45% |
| 192 | s11 | SNP | 35% |
| 193 | s11 | SNP | 35% |
| 194 | s12 | REF | 35% |
| 195 | s12 | SNP | 50% |
| 196 | s12 | REF | 50% |
| 197 | s12 | REF | 35% |
| 198 | s12 | SNP | 35% |
| 199 | s12 | REF | 35% |
| 200 | s12 | REF | 50% |
| 201 | s12 | SNP | 50% |
| 202 | s12 | REF | 50% |
| 203 | s12 | REF | 40% |
| 204 | s12 | SNP | 50% |
| 205 | s12 | REF | 50% |
| 206 | s12 | SNP | 40% |
| 207 | s12 | REF | 35% |
| 208 | s12 | REF | 40% |
| 209 | s12 | REF | 35% |
| 210 | s12 | SNP | 35% |
| 211 | s12 | SNP | 35% |
| 212 | s13 | REF | 35% |
| 213 | s13 | SNP | 40% |
| 214 | s13 | SNP | 35% |
| 215 | s14 | REF | 55% |
| 216 | s14 | SNP | 60% |
| 217 | s14 | SNP | 55% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 218 | s14 | REF | 65% |
| 219 | s14 | SNP | 70% |
| 220 | s14 | SNP | 60% |
| 221 | s14 | REF | 55% |
| 222 | s14 | REF | 70% |
| 223 | s15 | REF | 55% |
| 224 | s15 | SNP | 60% |
| 225 | s15 | SNP | 35% |
| 226 | s15 | REF | 35% |
| 227 | s15 | SNP | 40% |
| 228 | s15 | SNP | 40% |
| 229 | s15 | REF | 55% |
| 230 | s15 | SNP | 60% |
| 231 | s16 | SNP | 70% |
| 232 | s16 | REF | 75% |
| 233 | s16 | SNP | 65% |
| 234 | s16 | REF | 70% |
| 235 | s16 | SNP | 60% |
| 236 | s16 | REF | 65% |
| 237 | s16 | SNP | 60% |
| 238 | s16 | REF | 65% |
| 239 | s16 | REF | 85% |
| 240 | s16 | SNP | 80% |
| 241 | s16 | SNP | 65% |
| 242 | s16 | REF | 70% |
| 243 | s16 | SNP | 70% |
| 244 | s16 | REF | 75% |
| 245 | s16 | REF | 70% |
| 246 | s16 | SNP | 65% |
| 247 | s16 | REF | 70% |
| 248 | s16 | SNP | 65% |
| 249 | s16 | SNP | 65% |
| 250 | s16 | REF | 70% |
| 251 | s16 | REF | 70% |
| 252 | s16 | SNP | 65% |
| 253 | s16 | REF | 65% |
| 254 | s16 | SNP | 60% |
| 255 | s16 | SNP | 70% |
| 256 | s16 | REF | 75% |
| 257 | s16 | REF | 70% |
| 258 | s16 | SNP | 65% |
| 259 | s16 | SNP | 65% |
| 260 | s16 | REF | 70% |
| 261 | s16 | REF | 65% |
| 262 | s16 | SNP | 60% |
| 263 | s16 | SNP | 65% |
| 264 | s16 | REF | 70% |
| 265 | s17 | REF | 65% |
| 266 | s17 | REF | 50% |
| 267 | s17 | SNP | 50% |
| 268 | s17 | SNP | 50% |
| 269 | s17 | SNP | 45% |
| 270 | s17 | SNP | 45% |
| 271 | s17 | REF | 50% |
| 272 | s17 | SNP | 55% |
| 273 | s17 | SNP | 45% |
| 274 | s18 | REF | 60% |
| 275 | s18 | SNP | 65% |
| 276 | s18 | REF | 60% |
| 277 | s18 | SNP | 65% |
| 278 | s18 | SNP | 65% |
| 279 | s18 | REF | 60% |
| 280 | s18 | REF | 60% |
| 281 | s18 | SNP | 65% |
| 282 | s18 | SNP | 65% |
| 283 | s18 | SNP | 65% |
| 284 | s18 | REF | 60% |
| 285 | s18 | REF | 60% |
| 286 | s18 | SNP | 65% |
| 287 | s18 | SNP | 70% |
| 288 | s18 | SNP | 60% |
| 289 | s18 | SNP | 60% |
| 290 | s18 | REF | 55% |
| 291 | s19 | SNP | 55% |
| 292 | s19 | REF | 55% |
| 293 | s19 | REF | 50% |
| 294 | s19 | SNP | 50% |
| 295 | s19 | REF | 50% |
| 296 | s19 | SNP | 55% |
| 297 | s19 | REF | 55% |
| 298 | s19 | REF | 60% |
| 299 | s19 | REF | 45% |
| 300 | s19 | SNP | 45% |
| 301 | s19 | REF | 55% |
| 302 | s19 | SNP | 60% |
| 303 | s19 | SNP | 55% |
| 304 | s19 | SNP | 50% |
| 305 | s19 | REF | 50% |
| 306 | s19 | SNP | 50% |
| 307 | s19 | REF | 55% |
| 308 | s19 | REF | 55% |
| 309 | s19 | REF | 45% |
| 310 | s19 | SNP | 45% |
| 311 | s19 | SNP | 50% |
| 312 | s19 | REF | 50% |
| 313 | s20 | REF | 60% |
| 314 | s20 | SNP | 65% |
| 315 | s20 | REF | 60% |
| 316 | s20 | SNP | 70% |
| 317 | s20 | REF | 65% |
| 318 | s20 | SNP | 70% |
| 319 | s20 | REF | 65% |
| 320 | s20 | REF | 60% |
| 321 | s20 | REF | 60% |
| 322 | s20 | SNP | 70% |
| 323 | s20 | SNP | 65% |
| 324 | s20 | REF | 65% |
| 325 | s20 | SNP | 70% |
| 326 | s20 | SNP | 70% |
| 327 | s20 | REF | 65% |
| 328 | s20 | REF | 65% |
| 329 | s20 | REF | 60% |
| 330 | s20 | SNP | 65% |
| 331 | s20 | REF | 65% |
| 332 | s20 | SNP | 70% |
| 333 | s21 | REF | 45% |
| 334 | s21 | SNP | 50% |
| 335 | s21 | REF | 45% |
| 336 | s21 | SNP | 50% |
| 337 | s21 | SNP | 50% |
| 338 | s21 | REF | 45% |
| 339 | s21 | REF | 45% |
| 340 | s21 | SNP | 50% |
| 341 | s21 | REF | 50% |
| 342 | s21 | SNP | 55% |
| 343 | s21 | SNP | 50% |
| 344 | s21 | REF | 45% |
| 345 | s21 | SNP | 45% |
| 346 | s21 | REF | 40% |
| 347 | s22 | REF | 45% |
| 348 | s22 | SNP | 40% |
| 349 | s22 | SNP | 45% |
| 350 | s22 | SNP | 45% |
| 351 | s22 | REF | 50% |
| 352 | s22 | REF | 50% |
| 353 | s22 | SNP | 45% |
| 354 | s22 | REF | 55% |
| 355 | s22 | REF | 50% |
| 356 | s22 | SNP | 45% |
| 357 | s22 | REF | 50% |
| 358 | s22 | REF | 50% |
| 359 | s22 | SNP | 50% |
| 360 | s22 | REF | 50% |
| 361 | s23 | SNP | 55% |
| 362 | s23 | SNP | 55% |
| 363 | s23 | REF | 60% |
| 364 | s23 | SNP | 60% |
| 365 | s23 | REF | 65% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 366 | s23 | SNP | 60% |
| 367 | s23 | SNP | 60% |
| 368 | s23 | SNP | 60% |
| 369 | s23 | REF | 65% |
| 370 | s23 | REF | 60% |
| 371 | s23 | SNP | 55% |
| 372 | s23 | REF | 60% |
| 373 | s23 | SNP | 55% |
| 374 | s23 | SNP | 60% |
| 375 | s23 | SNP | 55% |
| 376 | s23 | SNP | 55% |
| 377 | s23 | REF | 60% |
| 378 | s23 | REF | 60% |
| 379 | s23 | SNP | 55% |
| 380 | s39 | SNP | 65% |
| 381 | s39 | SNP | 70% |
| 382 | s39 | SNP | 70% |
| 383 | s39 | SNP | 70% |
| 384 | s39 | SNP | 75% |
| 385 | s39 | SNP | 70% |
| 386 | s39 | SNP | 65% |
| 387 | s24 | SNP | 70% |
| 388 | s24 | SNP | 60% |
| 389 | s24 | SNP | 65% |
| 390 | s24 | REF | 65% |
| 391 | s24 | SNP | 70% |
| 392 | s24 | SNP | 70% |
| 393 | s24 | SNP | 60% |
| 394 | s24 | SNP | 55% |
| 395 | s24 | SNP | 65% |
| 396 | s24 | SNP | 55% |
| 397 | s24 | SNP | 60% |
| 398 | s24 | SNP | 65% |
| 399 | s24 | SNP | 70% |
| 400 | s25 | SNP | 55% |
| 401 | s25 | REF | 60% |
| 402 | s25 | REF | 45% |
| 403 | s25 | SNP | 40% |
| 404 | s25 | REF | 65% |
| 405 | s25 | SNP | 60% |
| 406 | s25 | REF | 70% |
| 407 | s25 | SNP | 55% |
| 408 | s25 | REF | 60% |
| 409 | s25 | SNP | 65% |
| 410 | s25 | SNP | 65% |
| 411 | s25 | REF | 70% |
| 412 | s25 | REF | 75% |
| 413 | s25 | REF | 65% |
| 414 | s25 | SNP | 60% |
| 415 | s25 | REF | 50% |
| 416 | s25 | SNP | 45% |
| 417 | s25 | REF | 60% |
| 418 | s25 | SNP | 55% |
| 419 | s25 | REF | 60% |
| 420 | s25 | SNP | 55% |
| 421 | s25 | REF | 65% |
| 422 | s25 | SNP | 60% |
| 423 | s25 | SNP | 70% |
| 424 | s26 | SNP | 35% |
| 425 | s26 | REF | 35% |
| 426 | s26 | SNP | 35% |
| 427 | s26 | REF | 35% |
| 428 | s26 | SNP | 35% |
| 429 | s26 | SNP | 35% |
| 430 | s26 | REF | 35% |
| 431 | s26 | REF | 35% |
| 432 | s26 | SNP | 35% |
| 433 | s26 | REF | 40% |
| 434 | s26 | REF | 35% |
| 435 | s26 | REF | 35% |
| 436 | s73 | SNP | 50% |
| 437 | s27 | REF | 80% |
| 438 | s27 | REF | 80% |
| 439 | s27 | SNP | 85% |
| 440 | s27 | REF | 75% |
| 441 | s27 | SNP | 80% |
| 442 | s27 | REF | 80% |
| 443 | s27 | REF | 75% |
| 444 | s27 | SNP | 80% |
| 445 | s27 | REF | 80% |
| 446 | s27 | SNP | 85% |
| 447 | s27 | SNP | 85% |
| 448 | s27 | SNP | 80% |
| 449 | s27 | SNP | 85% |
| 450 | s27 | REF | 80% |
| 451 | s27 | REF | 75% |
| 452 | s27 | SNP | 85% |
| 453 | s27 | REF | 80% |
| 454 | s27 | REF | 80% |
| 455 | s27 | SNP | 85% |
| 456 | s27 | SNP | 85% |
| 457 | s27 | SNP | 80% |
| 458 | s27 | REF | 75% |
| 459 | s27 | REF | 80% |
| 460 | s27 | SNP | 85% |
| 461 | s27 | REF | 75% |
| 462 | s27 | SNP | 85% |
| 463 | s27 | REF | 80% |
| 464 | s27 | REF | 80% |
| 465 | s27 | SNP | 85% |
| 466 | s4 | SNP | 45% |
| 467 | s4 | SNP | 45% |
| 468 | s4 | SNP | 40% |
| 469 | s28 | REF | 70% |
| 470 | s28 | SNP | 65% |
| 471 | s28 | SNP | 65% |
| 472 | s28 | REF | 70% |
| 473 | s28 | SNP | 65% |
| 474 | s28 | REF | 70% |
| 475 | s28 | SNP | 65% |
| 476 | s28 | SNP | 65% |
| 477 | s28 | REF | 70% |
| 478 | s28 | SNP | 65% |
| 479 | s28 | SNP | 65% |
| 480 | s28 | SNP | 65% |
| 481 | s28 | SNP | 65% |
| 482 | s28 | SNP | 65% |
| 483 | s28 | REF | 70% |
| 484 | s3 | SNP | 45% |
| 485 | s3 | SNP | 45% |
| 486 | s3 | SNP | 40% |
| 487 | s30 | REF | 45% |
| 488 | s30 | SNP | 50% |
| 489 | s30 | REF | 35% |
| 490 | s30 | SNP | 40% |
| 491 | s30 | REF | 50% |
| 492 | s30 | SNP | 55% |
| 493 | s30 | REF | 40% |
| 494 | s30 | SNP | 45% |
| 495 | s30 | SNP | 40% |
| 496 | s30 | REF | 35% |
| 497 | s30 | SNP | 45% |
| 498 | s30 | REF | 40% |
| 499 | s31 | REF | 70% |
| 500 | s31 | REF | 50% |
| 501 | s31 | SNP | 55% |
| 502 | s31 | REF | 65% |
| 503 | s31 | SNP | 70% |
| 504 | s31 | SNP | 75% |
| 505 | s31 | REF | 50% |
| 506 | s31 | SNP | 55% |
| 507 | s31 | REF | 75% |
| 508 | s31 | SNP | 55% |
| 509 | s31 | SNP | 50% |
| 510 | s31 | SNP | 55% |
| 511 | s31 | REF | 50% |
| 512 | s31 | REF | 70% |
| 513 | s31 | REF | 65% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 514 | s31 | SNP | 70% |
| 515 | s31 | REF | 55% |
| 516 | s31 | SNP | 60% |
| 517 | s31 | REF | 65% |
| 518 | s31 | SNP | 70% |
| 519 | s31 | SNP | 70% |
| 520 | s31 | SNP | 70% |
| 521 | s31 | REF | 65% |
| 522 | s31 | SNP | 75% |
| 523 | s31 | REF | 70% |
| 524 | s31 | REF | 60% |
| 525 | s31 | SNP | 65% |
| 526 | s31 | REF | 65% |
| 527 | s31 | REF | 50% |
| 528 | s31 | REF | 55% |
| 529 | s31 | SNP | 60% |
| 530 | s32 | SNP | 60% |
| 531 | s32 | SNP | 65% |
| 532 | s32 | SNP | 70% |
| 533 | s32 | REF | 75% |
| 534 | s32 | SNP | 65% |
| 535 | s32 | REF | 75% |
| 536 | s32 | SNP | 65% |
| 537 | s32 | REF | 70% |
| 538 | s32 | REF | 70% |
| 539 | s32 | SNP | 65% |
| 540 | s32 | SNP | 65% |
| 541 | s32 | REF | 70% |
| 542 | s32 | SNP | 65% |
| 543 | s32 | REF | 70% |
| 544 | s32 | REF | 75% |
| 545 | s74 | SNP | 65% |
| 546 | s74 | SNP | 65% |
| 547 | s74 | SNP | 65% |
| 548 | s33 | REF | 50% |
| 549 | s33 | SNP | 55% |
| 550 | s33 | REF | 40% |
| 551 | s33 | SNP | 45% |
| 552 | s33 | REF | 55% |
| 553 | s33 | SNP | 60% |
| 554 | s33 | REF | 40% |
| 555 | s33 | REF | 45% |
| 556 | s33 | REF | 60% |
| 557 | s33 | SNP | 65% |
| 558 | s33 | SNP | 65% |
| 559 | s33 | REF | 60% |
| 560 | s33 | SNP | 50% |
| 561 | s33 | SNP | 60% |
| 562 | s33 | REF | 55% |
| 563 | s33 | REF | 40% |
| 564 | s33 | SNP | 45% |
| 565 | s33 | SNP | 60% |
| 566 | s33 | REF | 55% |
| 567 | s33 | REF | 35% |
| 568 | s33 | SNP | 40% |
| 569 | s33 | SNP | 55% |
| 570 | s33 | REF | 50% |
| 571 | s33 | SNP | 60% |
| 572 | s33 | REF | 55% |
| 573 | s34 | SNP | 35% |
| 574 | s34 | REF | 50% |
| 575 | s34 | SNP | 45% |
| 576 | s34 | SNP | 50% |
| 577 | s34 | REF | 55% |
| 578 | s34 | SNP | 50% |
| 579 | s34 | REF | 55% |
| 580 | s34 | REF | 50% |
| 581 | s34 | SNP | 45% |
| 582 | s34 | REF | 50% |
| 583 | s34 | SNP | 45% |
| 584 | s35 | SNP | 70% |
| 585 | s35 | REF | 75% |
| 586 | s35 | REF | 75% |
| 587 | s35 | SNP | 70% |
| 588 | s35 | SNP | 70% |
| 589 | s35 | REF | 75% |
| 590 | s35 | REF | 85% |
| 591 | s35 | SNP | 80% |
| 592 | s35 | SNP | 75% |
| 593 | s35 | REF | 80% |
| 594 | s35 | REF | 75% |
| 595 | s35 | SNP | 70% |
| 596 | s35 | SNP | 85% |
| 597 | s35 | REF | 90% |
| 598 | s35 | REF | 85% |
| 599 | s35 | SNP | 80% |
| 600 | s35 | REF | 80% |
| 601 | s35 | SNP | 75% |
| 602 | s35 | SNP | 80% |
| 603 | s35 | REF | 85% |
| 604 | s35 | SNP | 70% |
| 605 | s35 | REF | 75% |
| 606 | s35 | REF | 75% |
| 607 | s35 | SNP | 70% |
| 608 | s35 | SNP | 80% |
| 609 | s35 | REF | 85% |
| 610 | s35 | SNP | 75% |
| 611 | s35 | REF | 80% |
| 612 | s35 | REF | 75% |
| 613 | s35 | SNP | 70% |
| 614 | s35 | SNP | 80% |
| 615 | s35 | REF | 85% |
| 616 | s35 | REF | 80% |
| 617 | s35 | SNP | 75% |
| 618 | s35 | REF | 80% |
| 619 | s35 | SNP | 75% |
| 620 | s35 | REF | 75% |
| 621 | s35 | SNP | 70% |
| 622 | s36 | SNP | 60% |
| 623 | s36 | REF | 65% |
| 624 | s36 | SNP | 70% |
| 625 | s36 | SNP | 65% |
| 626 | s36 | REF | 70% |
| 627 | s36 | SNP | 65% |
| 628 | s36 | SNP | 70% |
| 629 | s36 | SNP | 70% |
| 630 | s36 | SNP | 70% |
| 631 | s36 | SNP | 65% |
| 632 | s36 | SNP | 60% |
| 633 | s36 | REF | 65% |
| 634 | s36 | SNP | 65% |
| 635 | s36 | SNP | 65% |
| 636 | s36 | SNP | 65% |
| 637 | s36 | SNP | 65% |
| 638 | s36 | SNP | 65% |
| 639 | s36 | SNP | 70% |
| 640 | s29 | SNP | 70% |
| 641 | s29 | SNP | 70% |
| 642 | s29 | SNP | 75% |
| 643 | s29 | SNP | 75% |
| 644 | s29 | SNP | 65% |
| 645 | s29 | REF | 65% |
| 646 | s40 | SNP | 40% |
| 647 | s41 | SNP | 55% |
| 648 | s41 | REF | 60% |
| 649 | s41 | SNP | 65% |
| 650 | s41 | REF | 70% |
| 651 | s41 | REF | 75% |
| 652 | s41 | SNP | 70% |
| 653 | s41 | SNP | 60% |
| 654 | s41 | REF | 65% |
| 655 | s41 | REF | 60% |
| 656 | s41 | SNP | 65% |
| 657 | s41 | REF | 70% |
| 658 | s41 | SNP | 75% |
| 659 | s41 | REF | 80% |
| 660 | s41 | SNP | 55% |
| 661 | s41 | REF | 65% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 662 | s41 | SNP | 60% |
| 663 | s41 | SNP | 60% |
| 664 | s41 | REF | 65% |
| 665 | s41 | SNP | 55% |
| 666 | s41 | REF | 60% |
| 667 | s41 | SNP | 75% |
| 668 | s41 | REF | 80% |
| 669 | s42 | SNP | 65% |
| 670 | s42 | REF | 80% |
| 671 | s42 | SNP | 65% |
| 672 | s42 | SNP | 65% |
| 673 | s42 | REF | 70% |
| 674 | s42 | REF | 65% |
| 675 | s42 | SNP | 60% |
| 676 | s2 | SNP | 60% |
| 677 | s45 | SNP | 40% |
| 678 | s45 | REF | 45% |
| 679 | s45 | SNP | 40% |
| 680 | s45 | REF | 45% |
| 681 | s45 | SNP | 50% |
| 682 | s45 | REF | 55% |
| 683 | s45 | REF | 45% |
| 684 | s45 | SNP | 40% |
| 685 | s45 | REF | 45% |
| 686 | s76 | SNP | 50% |
| 687 | s76 | SNP | 50% |
| 688 | s46 | REF | 65% |
| 689 | s46 | SNP | 60% |
| 690 | s46 | REF | 65% |
| 691 | s46 | REF | 70% |
| 692 | s46 | SNP | 65% |
| 693 | s46 | SNP | 70% |
| 694 | s46 | REF | 75% |
| 695 | s46 | SNP | 65% |
| 696 | s46 | REF | 70% |
| 697 | s46 | SNP | 65% |
| 698 | s46 | REF | 70% |
| 699 | s46 | REF | 65% |
| 700 | s46 | SNP | 60% |
| 701 | s47 | SNP | 50% |
| 702 | s47 | SNP | 55% |
| 703 | s47 | REF | 80% |
| 704 | s47 | REF | 60% |
| 705 | s47 | SNP | 70% |
| 706 | s47 | REF | 75% |
| 707 | s47 | SNP | 65% |
| 708 | s47 | REF | 70% |
| 709 | s47 | REF | 65% |
| 710 | s47 | SNP | 60% |
| 711 | s47 | SNP | 75% |
| 712 | s47 | REF | 55% |
| 713 | s47 | REF | 60% |
| 714 | s47 | SNP | 55% |
| 715 | s48 | SNP | 55% |
| 716 | s48 | SNP | 65% |
| 717 | s48 | SNP | 65% |
| 718 | s48 | SNP | 65% |
| 719 | s48 | REF | 70% |
| 720 | s48 | REF | 70% |
| 721 | s48 | SNP | 65% |
| 722 | s48 | REF | 70% |
| 723 | s48 | SNP | 60% |
| 724 | s48 | REF | 70% |
| 725 | s48 | SNP | 55% |
| 726 | s48 | SNP | 60% |
| 727 | s48 | REF | 70% |
| 728 | s48 | REF | 70% |
| 729 | s48 | SNP | 65% |
| 730 | s48 | SNP | 50% |
| 731 | s48 | SNP | 50% |
| 732 | s48 | SNP | 60% |
| 733 | s48 | SNP | 65% |
| 734 | s49 | SNP | 55% |
| 735 | s49 | REF | 50% |
| 736 | s49 | SNP | 55% |
| 737 | s49 | REF | 50% |
| 738 | s49 | REF | 50% |
| 739 | s49 | SNP | 55% |
| 740 | s49 | REF | 50% |
| 741 | s49 | REF | 55% |
| 742 | s49 | SNP | 60% |
| 743 | s1, s2, s3, s4 | BOTH, REF, REF, BOTH | 60% |
| 744 | s1, s2, s3, s4 | BOTH, REF, BOTH, BOTH | 60% |
| 745 | s1, s2, s3, s4 | BOTH, REF, REF, REF | 55% |
| 746 | s1, s2, s3, s4 | BOTH, REF, REF, REF | 60% |
| 747 | s1, s2, s3, s4 | REF, REF, REF, REF | 45% |
| 748 | s1, s2, s3, s4 | REF, REF, REF, REF | 50% |
| 749 | s1, s2, s3, s4 | REF, REF, REF, REF | 55% |
| 750 | s1, s2, s3, s4 | REF, REF, REF, REF | 45% |
| 751 | s1, s2, s3, s4 | REF, REF, REF, REF | 55% |
| 752 | s5, s6 | REF, BOTH | 40% |
| 753 | s5, s6 | REF, BOTH | 40% |
| 754 | s5, s6 | REF, BOTH | 35% |
| 755 | s5, s6 | REF, BOTH | 35% |
| 756 | s5, s6 | REF, BOTH | 35% |
| 757 | s5, s6 | REF, BOTH | 35% |
| 758 | s5, s6 | REF, BOTH | 35% |
| 759 | s5, s6, s7 | REF, BOTH, BOTH | 35% |
| 760 | s5, s6, s7 | REF, BOTH, BOTH | 40% |
| 761 | s8 | BOTH | 40% |
| 762 | s8 | BOTH | 50% |
| 763 | s8 | BOTH | 40% |
| 764 | s9 | BOTH | 60% |
| 765 | s9 | BOTH | 50% |
| 766 | s9 | BOTH | 55% |
| 767 | s9 | BOTH | 50% |
| 768 | s10 | BOTH | 70% |
| 769 | s10 | BOTH | 65% |
| 770 | s10 | BOTH | 65% |
| 771 | s10 | BOTH | 65% |
| 772 | s11 | BOTH | 50% |
| 773 | s11 | BOTH | 45% |
| 774 | s12 | BOTH | 55% |
| 775 | s12 | BOTH | 45% |
| 776 | s12 | BOTH | 45% |
| 777 | s12 | BOTH | 40% |
| 778 | s12 | BOTH | 60% |
| 779 | s12 | BOTH | 60% |
| 780 | s13 | BOTH | 45% |
| 781 | s13 | BOTH | 50% |
| 782 | s13 | BOTH | 50% |
| 783 | s13 | BOTH | 35% |
| 784 | s14 | BOTH | 65% |
| 785 | s14 | BOTH | 60% |
| 786 | s14 | BOTH | 50% |
| 787 | s15 | BOTH | 35% |
| 788 | s15 | BOTH | 40% |
| 789 | s16 | BOTH | 65% |
| 790 | s16 | BOTH | 70% |
| 791 | s16 | BOTH | 80% |
| 792 | s18 | BOTH | 55% |
| 793 | s18 | BOTH | 55% |
| 794 | s18 | BOTH | 60% |
| 795 | s19 | BOTH | 55% |
| 796 | s19 | BOTH | 55% |
| 797 | s19 | BOTH | 60% |
| 798 | s19 | BOTH | 60% |
| 799 | s20 | BOTH | 70% |
| 800 | s20 | BOTH | 65% |
| 801 | s21 | BOTH | 55% |
| 802 | s21 | BOTH | 60% |
| 803 | s21 | BOTH | 50% |
| 804 | s21 | BOTH | 45% |
| 805 | s22 | BOTH | 50% |
| 806 | s22 | BOTH | 55% |
| 807 | s22 | BOTH | 50% |
| 808 | s22 | BOTH | 50% |
| 809 | s22 | BOTH | 50% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 810 | s22 | BOTH | 50% |
| 811 | s23 | BOTH | 60% |
| 812 | s23 | BOTH | 60% |
| 813 | s23 | BOTH | 70% |
| 814 | s23 | BOTH | 65% |
| 815 | s24 | BOTH | 60% |
| 816 | s24 | BOTH | 60% |
| 817 | s24 | BOTH | 60% |
| 818 | s24 | BOTH | 60% |
| 819 | s25 | BOTH | 50% |
| 820 | s25 | BOTH | 50% |
| 821 | s25 | BOTH | 75% |
| 822 | s25 | BOTH | 50% |
| 823 | s25 | BOTH | 50% |
| 824 | s26 | BOTH | 40% |
| 825 | s26 | BOTH | 40% |
| 826 | s26 | BOTH | 40% |
| 827 | s26 | BOTH | 45% |
| 828 | s27 | BOTH | 80% |
| 829 | s27 | BOTH | 85% |
| 830 | s27 | BOTH | 80% |
| 831 | s27 | BOTH | 85% |
| 832 | s27 | BOTH | 80% |
| 833 | s28 | BOTH | 65% |
| 834 | s28 | BOTH | 70% |
| 835 | s28, s29 | BOTH, REF | 65% |
| 836 | s28, s29 | REF, BOTH | 70% |
| 837 | s30 | BOTH | 60% |
| 838 | s30 | BOTH | 60% |
| 839 | s30 | BOTH | 65% |
| 840 | s30 | BOTH | 35% |
| 841 | s30 | BOTH | 60% |
| 842 | s31 | BOTH | 50% |
| 843 | s31 | BOTH | 75% |
| 844 | s31 | BOTH | 50% |
| 845 | s32 | BOTH | 70% |
| 846 | s32 | BOTH | 70% |
| 847 | s32 | BOTH | 70% |
| 848 | s32 | BOTH | 60% |
| 849 | s33 | BOTH | 35% |
| 850 | s33 | BOTH | 35% |
| 851 | s34 | BOTH | 45% |
| 852 | s34 | BOTH | 45% |
| 853 | s34 | BOTH | 45% |
| 854 | s35 | BOTH | 90% |
| 855 | s35 | BOTH | 75% |
| 856 | s35 | BOTH | 80% |
| 857 | s35 | BOTH | 80% |
| 858 | s35 | BOTH | 85% |
| 859 | s36, s24 | REF, BOTH | 65% |
| 860 | s36, s24 | REF, REF | 70% |
| 861 | s36, s24 | REF, REF | 65% |
| 862 | s36, s24 | REF, REF | 75% |
| 863 | s36, s24 | REF, REF | 65% |
| 864 | s36, s24 | REF, REF | 70% |
| 865 | s36, s24 | REF, REF | 75% |
| 866 | s36, s24 | REF, REF | 65% |
| 867 | s36, s24 | REF, REF | 75% |
| 868 | s36, s24 | REF, REF | 65% |
| 869 | s36, s24 | REF, REF | 75% |
| 870 | s36, s24 | REF, REF | 75% |
| 871 | s36, s24 | REF, REF | 60% |
| 872 | s36, s24 | REF, REF | 60% |
| 873 | s36, s24 | REF, REF | 65% |
| 874 | s36, s24 | BOTH, REF | 60% |
| 875 | s36 | BOTH | 60% |
| 876 | s36 | BOTH | 60% |
| 877 | s36 | BOTH | 60% |
| 878 | s36 | BOTH | 65% |
| 879 | s7, s37 | SNP, SNP | 50% |
| 880 | s7, s38 | SNP, SNP | 50% |
| 881 | s29, s39 | REF, BOTH | 65% |
| 882 | s29, s39 | REF, BOTH | 65% |
| 883 | s29, s39 | REF, REF | 65% |
| 884 | s29, s39 | REF, REF | 75% |
| 885 | s29, s39 | REF, REF | 75% |
| 886 | s29, s39 | REF, REF | 75% |
| 887 | s29, s39 | REF, REF | 75% |
| 888 | s29 | BOTH | 70% |
| 889 | s29 | BOTH | 70% |
| 890 | s40 | BOTH | 40% |
| 891 | s40 | BOTH | 45% |
| 892 | s40 | BOTH | 45% |
| 893 | s40 | BOTH | 40% |
| 894 | s41 | BOTH | 75% |
| 895 | s41 | BOTH | 60% |
| 896 | s41 | BOTH | 80% |
| 897 | s41 | BOTH | 75% |
| 898 | s41 | BOTH | 60% |
| 899 | s42 | BOTH | 55% |
| 900 | s42 | BOTH | 80% |
| 901 | s43 | BOTH | 50% |
| 902 | s43 | BOTH | 55% |
| 903 | s43 | BOTH | 55% |
| 904 | s43 | BOTH | 60% |
| 905 | s43 | BOTH | 55% |
| 906 | s43 | BOTH | 60% |
| 907 | s44 | BOTH | 50% |
| 908 | s44 | BOTH | 55% |
| 909 | s44 | BOTH | 50% |
| 910 | s44 | BOTH | 55% |
| 911 | s2, s3, s4 | REF, REF, REF | 40% |
| 912 | s2, s3, s4 | REF, REF, REF | 35% |
| 913 | s2, s3, s4 | REF, REF, REF | 50% |
| 914 | s2, s3, s4 | REF, REF, REF | 60% |
| 915 | s2, s3, s4 | REF, REF, REF | 55% |
| 916 | s2, s3 | BOTH, BOTH | 65% |
| 917 | s2, s3 | REF, REF | 60% |
| 918 | s2 | BOTH | 65% |
| 919 | s45 | BOTH | 50% |
| 920 | s45 | BOTH | 50% |
| 921 | s45 | BOTH | 45% |
| 922 | s45 | BOTH | 45% |
| 923 | s45 | BOTH | 40% |
| 924 | s45 | BOTH | 45% |
| 925 | s46 | BOTH | 65% |
| 926 | s46 | BOTH | 55% |
| 927 | s46 | BOTH | 65% |
| 928 | s46 | BOTH | 65% |
| 929 | s46 | BOTH | 55% |
| 930 | s47 | BOTH | 50% |
| 931 | s47 | BOTH | 70% |
| 932 | s47 | BOTH | 45% |
| 933 | s48 | BOTH | 70% |
| 934 | s49 | BOTH | 60% |
| 935 | s49 | BOTH | 60% |
| 936 | s49 | BOTH | 60% |
| 937 | s49 | BOTH | 60% |
| 938 | s50 | BOTH | 75% |
| 939 | s50 | BOTH | 70% |
| 940 | s50 | BOTH | 70% |
| 941 | s50 | BOTH | 80% |
| 942 | s50 | BOTH | 70% |
| 943 | s51 | BOTH | 60% |
| 944 | s51 | BOTH | 75% |
| 945 | s51 | BOTH | 75% |
| 946 | s52 | BOTH | 80% |
| 947 | s52 | BOTH | 70% |
| 948 | s52 | BOTH | 80% |
| 949 | s52 | BOTH | 65% |
| 950 | s52 | BOTH | 75% |
| 951 | s53 | BOTH | 80% |
| 952 | s53 | BOTH | 50% |
| 953 | s53 | BOTH | 80% |
| 954 | s54 | BOTH | 75% |
| 955 | s54 | BOTH | 60% |
| 956 | s54 | BOTH | 70% |
| 957 | s54 | BOTH | 75% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 958 | s54 | BOTH | 70% |
| 959 | s55 | BOTH | 45% |
| 960 | s55 | BOTH | 55% |
| 961 | s55 | BOTH | 55% |
| 962 | s55 | BOTH | 55% |
| 963 | s55 | BOTH | 55% |
| 964 | s55 | BOTH | 50% |
| 965 | s56 | BOTH | 60% |
| 966 | s56 | BOTH | 60% |
| 967 | s56 | BOTH | 70% |
| 968 | s56 | BOTH | 50% |
| 969 | s57 | BOTH | 40% |
| 970 | s57 | BOTH | 45% |
| 971 | s57 | BOTH | 60% |
| 972 | s57 | BOTH | 60% |
| 973 | s57 | BOTH | 45% |
| 974 | s58 | BOTH | 45% |
| 975 | s58 | BOTH | 50% |
| 976 | s58 | BOTH | 50% |
| 977 | s58 | BOTH | 50% |
| 978 | s58 | BOTH | 40% |
| 979 | s58 | BOTH | 40% |
| 980 | s59 | BOTH | 50% |
| 981 | s59 | BOTH | 45% |
| 982 | s59 | BOTH | 40% |
| 983 | s60 | BOTH | 45% |
| 984 | s60 | BOTH | 45% |
| 985 | s60 | BOTH | 55% |
| 986 | s60 | BOTH | 60% |
| 987 | s60 | BOTH | 50% |
| 988 | s60 | BOTH | 50% |
| 989 | s61 | BOTH | 45% |
| 990 | s61 | BOTH | 50% |
| 991 | s61 | BOTH | 45% |
| 992 | s61 | BOTH | 55% |
| 993 | s61 | BOTH | 50% |
| 994 | s62 | BOTH | 50% |
| 995 | s62 | BOTH | 60% |
| 996 | s62 | BOTH | 50% |
| 997 | s62 | BOTH | 55% |
| 998 | s62 | BOTH | 55% |
| 999 | s63, s48 | REF, BOTH | 70% |
| 1000 | s63, s48 | REF, BOTH | 70% |
| 1001 | s63, s48 | REF, BOTH | 65% |
| 1002 | s63, s48 | BOTH, REF | 60% |
| 1003 | s63, s48 | BOTH, REF | 65% |
| 1004 | s63, s48 | BOTH, REF | 65% |
| 1005 | s63, s48 | REF, REF | 70% |
| 1006 | s63, s48 | REF, REF | 70% |
| 1007 | s63, s48 | REF, REF | 65% |
| 1008 | s63, s48 | REF, REF | 70% |
| 1009 | s63, s48 | REF, REF | 60% |
| 1010 | s63, s48 | REF, REF | 70% |
| 1011 | s63, s48 | REF, REF | 60% |
| 1012 | s63, s48 | REF, REF | 70% |
| 1013 | s63, s48 | REF, REF | 60% |
| 1014 | s63, s48 | REF, REF | 60% |
| 1015 | s63, s48 | REF, REF | 65% |
| 1016 | s63, s48 | REF, REF | 65% |
| 1017 | s63 | BOTH | 75% |
| 1018 | s64, s17 | REF, BOTH | 45% |
| 1019 | s64, s17 | REF, BOTH | 50% |
| 1020 | s64, s17 | REF, BOTH | 50% |
| 1021 | s64, s17 | REF, BOTH | 45% |
| 1022 | s64, s17 | BOTH, REF | 45% |
| 1023 | s64, s17 | BOTH, REF | 40% |
| 1024 | s64, s17 | REF, REF | 40% |
| 1025 | s64, s17 | REF, REF | 35% |
| 1026 | s64, s17 | REF, REF | 40% |
| 1027 | s64, s17 | REF, REF | 40% |
| 1028 | s64, s17 | REF, REF | 40% |
| 1029 | s64, s17 | REF, REF | 40% |
| 1030 | s64, s17 | REF, REF | 40% |
| 1031 | s64, s17 | REF, REF | 40% |
| 1032 | s64, s17 | REF, REF | 40% |
| 1033 | s64, s17 | REF, REF | 40% |
| 1034 | s64, s17 | REF, REF | 40% |
| 1035 | s64, s17 | REF, REF | 35% |
| 1036 | s64, s17 | REF, REF | 40% |
| 1037 | s64 | BOTH | 70% |
| 1038 | s65 | BOTH | 65% |
| 1039 | s65 | BOTH | 65% |
| 1040 | s66 | BOTH | 65% |
| 1041 | s66 | BOTH | 65% |
| 1042 | s66 | BOTH | 45% |
| 1043 | s66 | BOTH | 50% |
| 1044 | s66 | BOTH | 65% |
| 1045 | s66 | BOTH | 55% |
| 1046 | s67 | BOTH | 35% |
| 1047 | s67 | BOTH | 40% |
| 1048 | s67 | BOTH | 50% |
| 1049 | s67 | BOTH | 60% |
| 1050 | s67 | BOTH | 55% |
| 1051 | s68 | BOTH | 50% |
| 1052 | s68 | BOTH | 40% |
| 1053 | s68 | BOTH | 50% |
| 1054 | s1 | SNP | 45% |
| 1055 | s1 | SNP | 50% |
| 1056 | s1 | SNP | 45% |
| 1057 | s1 | SNP | 50% |
| 1058 | s5 | SNP | 40% |
| 1059 | s5 | SNP | 40% |
| 1060 | s5 | SNP | 35% |
| 1061 | s69 | SNP | 40% |
| 1062 | s8 | REF | 60% |
| 1063 | s8 | SNP | 65% |
| 1064 | s8 | REF | 40% |
| 1065 | s8 | SNP | 45% |
| 1066 | s8 | SNP | 45% |
| 1067 | s8 | SNP | 45% |
| 1068 | s8 | REF | 40% |
| 1069 | s8 | SNP | 50% |
| 1070 | s8 | REF | 45% |
| 1071 | s8 | REF | 50% |
| 1072 | s8 | REF | 40% |
| 1073 | s8 | SNP | 45% |
| 1074 | s8 | REF | 55% |
| 1075 | s8 | SNP | 60% |
| 1076 | s8 | SNP | 55% |
| 1077 | s8 | REF | 50% |
| 1078 | s8 | SNP | 60% |
| 1079 | s8 | REF | 55% |
| 1080 | s8 | SNP | 65% |
| 1081 | s8 | REF | 60% |
| 1082 | s8 | SNP | 45% |
| 1083 | s8 | SNP | 45% |
| 1084 | s8 | SNP | 45% |
| 1085 | s8 | REF | 40% |
| 1086 | s8 | REF | 40% |
| 1087 | s8 | SNP | 45% |
| 1088 | s8 | REF | 40% |
| 1089 | s8 | REF | 40% |
| 1090 | s8 | SNP | 60% |
| 1091 | s8 | SNP | 65% |
| 1092 | s8 | REF | 40% |
| 1093 | s8 | SNP | 45% |
| 1094 | s8 | SNP | 50% |
| 1095 | s8 | REF | 45% |
| 1096 | s8 | REF | 40% |
| 1097 | s8 | SNP | 45% |
| 1098 | s8 | REF | 40% |
| 1099 | s8 | SNP | 45% |
| 1100 | s8 | SNP | 65% |
| 1101 | s8 | SNP | 65% |
| 1102 | s8 | SNP | 55% |
| 1103 | s8 | SNP | 65% |
| 1104 | s8 | SNP | 65% |
| 1105 | s8 | REF | 60% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1106 | s8 | SNP | 55% |
| 1107 | s8 | SNP | 60% |
| 1108 | s8 | REF | 55% |
| 1109 | s8 | REF | 40% |
| 1110 | s8 | SNP | 65% |
| 1111 | s8 | REF | 60% |
| 1112 | s8 | SNP | 55% |
| 1113 | s8 | SNP | 65% |
| 1114 | s8 | REF | 60% |
| 1115 | s9 | REF | 60% |
| 1116 | s9 | SNP | 55% |
| 1117 | s9 | REF | 60% |
| 1118 | s9 | SNP | 55% |
| 1119 | s9 | SNP | 60% |
| 1120 | s9 | SNP | 60% |
| 1121 | s9 | REF | 65% |
| 1122 | s9 | REF | 60% |
| 1123 | s9 | SNP | 55% |
| 1124 | s9 | REF | 55% |
| 1125 | s9 | REF | 65% |
| 1126 | s9 | SNP | 60% |
| 1127 | s9 | REF | 65% |
| 1128 | s9 | SNP | 60% |
| 1129 | s9 | REF | 65% |
| 1130 | s9 | SNP | 60% |
| 1131 | s9 | REF | 65% |
| 1132 | s9 | REF | 65% |
| 1133 | s9 | SNP | 60% |
| 1134 | s9 | SNP | 60% |
| 1135 | s9 | REF | 70% |
| 1136 | s9 | SNP | 65% |
| 1137 | s9 | SNP | 65% |
| 1138 | s9 | REF | 70% |
| 1139 | s9 | REF | 65% |
| 1140 | s9 | SNP | 60% |
| 1141 | s9 | SNP | 60% |
| 1142 | s9 | REF | 65% |
| 1143 | s9 | SNP | 60% |
| 1144 | s9 | REF | 65% |
| 1145 | s9 | REF | 65% |
| 1146 | s9 | SNP | 60% |
| 1147 | s9 | SNP | 65% |
| 1148 | s9 | REF | 70% |
| 1149 | s9 | REF | 65% |
| 1150 | s9 | SNP | 60% |
| 1151 | s9 | REF | 65% |
| 1152 | s9 | SNP | 60% |
| 1153 | s9 | REF | 65% |
| 1154 | s9 | SNP | 60% |
| 1155 | s9 | SNP | 60% |
| 1156 | s9 | REF | 65% |
| 1157 | s9 | REF | 65% |
| 1158 | s9 | SNP | 50% |
| 1159 | s9 | SNP | 60% |
| 1160 | s9 | REF | 65% |
| 1161 | s9 | SNP | 60% |
| 1162 | s9 | SNP | 60% |
| 1163 | s9 | REF | 65% |
| 1164 | s9 | SNP | 60% |
| 1165 | s9 | SNP | 55% |
| 1166 | s9 | REF | 60% |
| 1167 | s70 | SNP | 65% |
| 1168 | s70 | SNP | 75% |
| 1169 | s70 | SNP | 80% |
| 1170 | s70 | SNP | 55% |
| 1171 | s70 | REF | 60% |
| 1172 | s70 | REF | 75% |
| 1173 | s70 | SNP | 70% |
| 1174 | s70 | REF | 75% |
| 1175 | s70 | REF | 70% |
| 1176 | s70 | SNP | 70% |
| 1177 | s70 | SNP | 75% |
| 1178 | s70 | REF | 65% |
| 1179 | s71 | SNP | 45% |
| 1180 | s71 | SNP | 65% |
| 1181 | s71 | SNP | 65% |
| 1182 | s71 | SNP | 55% |
| 1183 | s71 | SNP | 65% |
| 1184 | s71 | SNP | 45% |
| 1185 | s71 | SNP | 45% |
| 1186 | s71 | SNP | 50% |
| 1187 | s10 | REF | 65% |
| 1188 | s10 | SNP | 70% |
| 1189 | s10 | SNP | 75% |
| 1190 | s10 | REF | 70% |
| 1191 | s10 | SNP | 70% |
| 1192 | s10 | REF | 65% |
| 1193 | s10 | REF | 55% |
| 1194 | s10 | REF | 65% |
| 1195 | s10 | SNP | 70% |
| 1196 | s10 | SNP | 75% |
| 1197 | s10 | REF | 70% |
| 1198 | s10 | SNP | 75% |
| 1199 | s10 | REF | 70% |
| 1200 | s10 | REF | 55% |
| 1201 | s10 | SNP | 80% |
| 1202 | s10 | REF | 75% |
| 1203 | s10 | SNP | 70% |
| 1204 | s10 | SNP | 70% |
| 1205 | s10 | REF | 55% |
| 1206 | s10 | SNP | 60% |
| 1207 | s10 | REF | 65% |
| 1208 | s10 | SNP | 70% |
| 1209 | s10 | SNP | 80% |
| 1210 | s10 | SNP | 60% |
| 1211 | s10 | REF | 55% |
| 1212 | s10 | REF | 70% |
| 1213 | s10 | SNP | 75% |
| 1214 | s10 | SNP | 60% |
| 1215 | s10 | REF | 55% |
| 1216 | s10 | SNP | 60% |
| 1217 | s10 | REF | 65% |
| 1218 | s10 | REF | 65% |
| 1219 | s10 | SNP | 70% |
| 1220 | s10 | SNP | 75% |
| 1221 | s10 | REF | 70% |
| 1222 | s10 | SNP | 70% |
| 1223 | s10 | REF | 60% |
| 1224 | s10 | SNP | 65% |
| 1225 | s10 | REF | 65% |
| 1226 | s10 | REF | 65% |
| 1227 | s10 | SNP | 70% |
| 1228 | s10 | REF | 65% |
| 1229 | s10 | SNP | 70% |
| 1230 | s10 | REF | 65% |
| 1231 | s10 | SNP | 70% |
| 1232 | s10 | SNP | 75% |
| 1233 | s10 | SNP | 60% |
| 1234 | s10 | REF | 70% |
| 1235 | s10 | SNP | 75% |
| 1236 | s10 | REF | 55% |
| 1237 | s10 | SNP | 75% |
| 1238 | s10 | REF | 70% |
| 1239 | s10 | REF | 70% |
| 1240 | s10 | SNP | 75% |
| 1241 | s10 | SNP | 60% |
| 1242 | s10 | REF | 50% |
| 1243 | s10 | REF | 70% |
| 1244 | s10 | SNP | 75% |
| 1245 | s10 | SNP | 55% |
| 1246 | s10 | REF | 65% |
| 1247 | s10 | SNP | 70% |
| 1248 | s10 | REF | 65% |
| 1249 | s10 | REF | 65% |
| 1250 | s10 | REF | 60% |
| 1251 | s11 | SNP | 45% |
| 1252 | s11 | SNP | 55% |
| 1253 | s11 | REF | 50% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1254 | s11 | SNP | 35% |
| 1255 | s11 | REF | 55% |
| 1256 | s11 | SNP | 60% |
| 1257 | s11 | SNP | 35% |
| 1258 | s11 | SNP | 55% |
| 1259 | s11 | REF | 50% |
| 1260 | s11 | SNP | 35% |
| 1261 | s11 | SNP | 35% |
| 1262 | s11 | SNP | 40% |
| 1263 | s11 | SNP | 60% |
| 1264 | s11 | SNP | 35% |
| 1265 | s11 | SNP | 55% |
| 1266 | s11 | REF | 45% |
| 1267 | s11 | SNP | 50% |
| 1268 | s11 | REF | 60% |
| 1269 | s11 | SNP | 65% |
| 1270 | s11 | REF | 50% |
| 1271 | s11 | SNP | 55% |
| 1272 | s11 | REF | 55% |
| 1273 | s11 | SNP | 40% |
| 1274 | s11 | REF | 35% |
| 1275 | s11 | SNP | 35% |
| 1276 | s11 | SNP | 40% |
| 1277 | s11 | SNP | 65% |
| 1278 | s11 | REF | 60% |
| 1279 | s11 | REF | 55% |
| 1280 | s11 | SNP | 60% |
| 1281 | s11 | SNP | 35% |
| 1282 | s11 | SNP | 50% |
| 1283 | s11 | REF | 45% |
| 1284 | s11 | REF | 50% |
| 1285 | s11 | SNP | 55% |
| 1286 | s11 | SNP | 35% |
| 1287 | s11 | REF | 45% |
| 1288 | s11 | SNP | 50% |
| 1289 | s11 | SNP | 55% |
| 1290 | s11 | SNP | 35% |
| 1291 | s11 | SNP | 60% |
| 1292 | s11 | REF | 55% |
| 1293 | s11 | REF | 50% |
| 1294 | s11 | SNP | 35% |
| 1295 | s11 | SNP | 35% |
| 1296 | s11 | SNP | 35% |
| 1297 | s12 | SNP | 50% |
| 1298 | s12 | SNP | 55% |
| 1299 | s12 | SNP | 45% |
| 1300 | s12 | REF | 45% |
| 1301 | s12 | SNP | 50% |
| 1302 | s12 | REF | 50% |
| 1303 | s12 | SNP | 50% |
| 1304 | s12 | REF | 50% |
| 1305 | s12 | REF | 45% |
| 1306 | s12 | SNP | 45% |
| 1307 | s12 | REF | 50% |
| 1308 | s12 | REF | 35% |
| 1309 | s12 | REF | 35% |
| 1310 | s12 | REF | 50% |
| 1311 | s12 | SNP | 50% |
| 1312 | s12 | REF | 40% |
| 1313 | s12 | REF | 55% |
| 1314 | s12 | SNP | 55% |
| 1315 | s12 | SNP | 50% |
| 1316 | s12 | REF | 50% |
| 1317 | s12 | SNP | 50% |
| 1318 | s12 | SNP | 55% |
| 1319 | s12 | REF | 55% |
| 1320 | s12 | REF | 50% |
| 1321 | s12 | SNP | 50% |
| 1322 | s12 | REF | 50% |
| 1323 | s12 | REF | 50% |
| 1324 | s12 | REF | 55% |
| 1325 | s12 | SNP | 55% |
| 1326 | s12 | SNP | 40% |
| 1327 | s12 | REF | 40% |
| 1328 | s12 | REF | 45% |
| 1329 | s12 | REF | 50% |
| 1330 | s12 | SNP | 50% |
| 1331 | s12 | REF | 35% |
| 1332 | s12 | SNP | 40% |
| 1333 | s12 | REF | 40% |
| 1334 | s12 | SNP | 45% |
| 1335 | s12 | REF | 45% |
| 1336 | s12 | REF | 55% |
| 1337 | s12 | REF | 50% |
| 1338 | s12 | SNP | 50% |
| 1339 | s12 | SNP | 50% |
| 1340 | s12 | REF | 50% |
| 1341 | s12 | REF | 35% |
| 1342 | s12 | SNP | 40% |
| 1343 | s12 | REF | 40% |
| 1344 | s12 | REF | 50% |
| 1345 | s12 | REF | 35% |
| 1346 | s12 | SNP | 35% |
| 1347 | s13 | REF | 40% |
| 1348 | s13 | REF | 40% |
| 1349 | s13 | SNP | 45% |
| 1350 | s13 | SNP | 35% |
| 1351 | s13 | REF | 40% |
| 1352 | s13 | SNP | 45% |
| 1353 | s13 | SNP | 45% |
| 1354 | s13 | SNP | 35% |
| 1355 | s13 | SNP | 35% |
| 1356 | s13 | REF | 35% |
| 1357 | s13 | SNP | 40% |
| 1358 | s13 | SNP | 35% |
| 1359 | s14 | SNP | 65% |
| 1360 | s14 | SNP | 60% |
| 1361 | s14 | REF | 70% |
| 1362 | s14 | REF | 55% |
| 1363 | s14 | SNP | 60% |
| 1364 | s14 | SNP | 70% |
| 1365 | s14 | REF | 65% |
| 1366 | s14 | REF | 60% |
| 1367 | s14 | SNP | 65% |
| 1368 | s14 | SNP | 65% |
| 1369 | s14 | SNP | 55% |
| 1370 | s14 | REF | 50% |
| 1371 | s14 | REF | 70% |
| 1372 | s14 | SNP | 75% |
| 1373 | s14 | REF | 50% |
| 1374 | s14 | REF | 60% |
| 1375 | s14 | SNP | 65% |
| 1376 | s14 | SNP | 75% |
| 1377 | s14 | SNP | 60% |
| 1378 | s14 | SNP | 65% |
| 1379 | s14 | SNP | 55% |
| 1380 | s14 | SNP | 75% |
| 1381 | s14 | REF | 60% |
| 1382 | s14 | SNP | 65% |
| 1383 | s14 | REF | 60% |
| 1384 | s14 | SNP | 65% |
| 1385 | s14 | SNP | 75% |
| 1386 | s14 | SNP | 65% |
| 1387 | s14 | SNP | 65% |
| 1388 | s14 | SNP | 75% |
| 1389 | s14 | REF | 70% |
| 1390 | s14 | SNP | 70% |
| 1391 | s14 | REF | 65% |
| 1392 | s14 | REF | 70% |
| 1393 | s14 | SNP | 75% |
| 1394 | s14 | SNP | 70% |
| 1395 | s14 | SNP | 70% |
| 1396 | s14 | REF | 65% |
| 1397 | s14 | REF | 70% |
| 1398 | s14 | REF | 65% |
| 1399 | s14 | SNP | 70% |
| 1400 | s14 | SNP | 65% |
| 1401 | s14 | REF | 60% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1402 | s14 | SNP | 55% |
| 1403 | s14 | SNP | 60% |
| 1404 | s14 | REF | 55% |
| 1405 | s14 | SNP | 65% |
| 1406 | s14 | REF | 60% |
| 1407 | s14 | REF | 70% |
| 1408 | s14 | SNP | 75% |
| 1409 | s14 | REF | 60% |
| 1410 | s14 | SNP | 65% |
| 1411 | s14 | REF | 70% |
| 1412 | s14 | SNP | 65% |
| 1413 | s14 | REF | 60% |
| 1414 | s14 | SNP | 70% |
| 1415 | s72 | SNP | 35% |
| 1416 | s15 | REF | 50% |
| 1417 | s15 | SNP | 55% |
| 1418 | s15 | REF | 55% |
| 1419 | s15 | SNP | 60% |
| 1420 | s15 | SNP | 50% |
| 1421 | s15 | REF | 45% |
| 1422 | s15 | REF | 45% |
| 1423 | s15 | SNP | 50% |
| 1424 | s15 | REF | 40% |
| 1425 | s15 | SNP | 45% |
| 1426 | s15 | REF | 35% |
| 1427 | s15 | REF | 50% |
| 1428 | s15 | SNP | 55% |
| 1429 | s15 | REF | 45% |
| 1430 | s15 | SNP | 50% |
| 1431 | s15 | SNP | 40% |
| 1432 | s15 | SNP | 40% |
| 1433 | s15 | REF | 40% |
| 1434 | s15 | SNP | 45% |
| 1435 | s15 | SNP | 45% |
| 1436 | s15 | REF | 60% |
| 1437 | s15 | SNP | 65% |
| 1438 | s15 | SNP | 50% |
| 1439 | s15 | REF | 45% |
| 1440 | s15 | SNP | 65% |
| 1441 | s15 | REF | 60% |
| 1442 | s15 | REF | 40% |
| 1443 | s15 | SNP | 60% |
| 1444 | s15 | SNP | 55% |
| 1445 | s15 | REF | 50% |
| 1446 | s15 | SNP | 35% |
| 1447 | s15 | SNP | 45% |
| 1448 | s15 | REF | 40% |
| 1449 | s15 | SNP | 60% |
| 1450 | s15 | REF | 55% |
| 1451 | s15 | REF | 40% |
| 1452 | s15 | SNP | 45% |
| 1453 | s15 | REF | 50% |
| 1454 | s15 | SNP | 55% |
| 1455 | s15 | REF | 45% |
| 1456 | s15 | SNP | 50% |
| 1457 | s15 | REF | 40% |
| 1458 | s15 | SNP | 45% |
| 1459 | s15 | REF | 35% |
| 1460 | s15 | SNP | 40% |
| 1461 | s15 | SNP | 60% |
| 1462 | s15 | REF | 55% |
| 1463 | s15 | REF | 35% |
| 1464 | s15 | SNP | 45% |
| 1465 | s15 | REF | 40% |
| 1466 | s15 | SNP | 60% |
| 1467 | s15 | REF | 55% |
| 1468 | s15 | REF | 35% |
| 1469 | s15 | SNP | 40% |
| 1470 | s15 | SNP | 60% |
| 1471 | s15 | REF | 55% |
| 1472 | s15 | SNP | 55% |
| 1473 | s15 | REF | 50% |
| 1474 | s16 | SNP | 75% |
| 1475 | s16 | REF | 80% |
| 1476 | s16 | REF | 85% |
| 1477 | s16 | SNP | 80% |
| 1478 | s16 | SNP | 80% |
| 1479 | s16 | SNP | 80% |
| 1480 | s16 | REF | 85% |
| 1481 | s16 | SNP | 65% |
| 1482 | s16 | REF | 70% |
| 1483 | s16 | SNP | 70% |
| 1484 | s16 | REF | 75% |
| 1485 | s16 | REF | 85% |
| 1486 | s16 | SNP | 80% |
| 1487 | s16 | REF | 85% |
| 1488 | s16 | SNP | 80% |
| 1489 | s16 | REF | 80% |
| 1490 | s16 | SNP | 75% |
| 1491 | s16 | REF | 75% |
| 1492 | s16 | SNP | 70% |
| 1493 | s16 | REF | 70% |
| 1494 | s16 | SNP | 65% |
| 1495 | s16 | REF | 75% |
| 1496 | s16 | SNP | 70% |
| 1497 | s16 | REF | 75% |
| 1498 | s16 | SNP | 65% |
| 1499 | s16 | REF | 70% |
| 1500 | s16 | SNP | 70% |
| 1501 | s16 | REF | 75% |
| 1502 | s16 | REF | 85% |
| 1503 | s16 | SNP | 70% |
| 1504 | s16 | SNP | 80% |
| 1505 | s16 | REF | 90% |
| 1506 | s16 | SNP | 85% |
| 1507 | s16 | REF | 70% |
| 1508 | s16 | REF | 85% |
| 1509 | s16 | REF | 80% |
| 1510 | s16 | SNP | 80% |
| 1511 | s16 | REF | 70% |
| 1512 | s16 | SNP | 65% |
| 1513 | s16 | SNP | 65% |
| 1514 | s17 | REF | 45% |
| 1515 | s17 | SNP | 45% |
| 1516 | s17 | SNP | 45% |
| 1517 | s17 | REF | 45% |
| 1518 | s17 | SNP | 40% |
| 1519 | s17 | SNP | 50% |
| 1520 | s17 | SNP | 50% |
| 1521 | s17 | REF | 45% |
| 1522 | s17 | REF | 45% |
| 1523 | s17 | SNP | 45% |
| 1524 | s17 | SNP | 45% |
| 1525 | s17 | SNP | 55% |
| 1526 | s17 | REF | 50% |
| 1527 | s17 | SNP | 70% |
| 1528 | s17 | SNP | 45% |
| 1529 | s17 | SNP | 45% |
| 1530 | s17 | SNP | 45% |
| 1531 | s17 | REF | 55% |
| 1532 | s17 | SNP | 45% |
| 1533 | s17 | SNP | 45% |
| 1534 | s17 | REF | 60% |
| 1535 | s17 | SNP | 65% |
| 1536 | s17 | REF | 60% |
| 1537 | s17 | SNP | 65% |
| 1538 | s17 | REF | 65% |
| 1539 | s17 | SNP | 70% |
| 1540 | s17 | REF | 70% |
| 1541 | s17 | REF | 60% |
| 1542 | s17 | REF | 45% |
| 1543 | s17 | SNP | 45% |
| 1544 | s17 | SNP | 65% |
| 1545 | s17 | REF | 65% |
| 1546 | s17 | SNP | 45% |
| 1547 | s17 | REF | 55% |
| 1548 | s17 | SNP | 45% |
| 1549 | s17 | REF | 40% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1550 | s17 | REF | 60% |
| 1551 | s17 | SNP | 40% |
| 1552 | s17 | SNP | 55% |
| 1553 | s17 | REF | 50% |
| 1554 | s17 | SNP | 45% |
| 1555 | s18 | REF | 60% |
| 1556 | s18 | SNP | 65% |
| 1557 | s18 | REF | 55% |
| 1558 | s18 | SNP | 60% |
| 1559 | s18 | REF | 65% |
| 1560 | s18 | SNP | 70% |
| 1561 | s18 | REF | 65% |
| 1562 | s18 | SNP | 70% |
| 1563 | s18 | REF | 55% |
| 1564 | s18 | REF | 65% |
| 1565 | s18 | SNP | 70% |
| 1566 | s18 | REF | 60% |
| 1567 | s18 | SNP | 65% |
| 1568 | s18 | REF | 60% |
| 1569 | s18 | SNP | 65% |
| 1570 | s18 | SNP | 70% |
| 1571 | s18 | SNP | 65% |
| 1572 | s18 | SNP | 65% |
| 1573 | s18 | SNP | 70% |
| 1574 | s18 | REF | 60% |
| 1575 | s18 | SNP | 75% |
| 1576 | s18 | REF | 70% |
| 1577 | s18 | REF | 70% |
| 1578 | s18 | SNP | 75% |
| 1579 | s18 | REF | 55% |
| 1580 | s18 | SNP | 60% |
| 1581 | s18 | SNP | 75% |
| 1582 | s18 | REF | 70% |
| 1583 | s18 | SNP | 70% |
| 1584 | s18 | REF | 65% |
| 1585 | s18 | SNP | 60% |
| 1586 | s18 | SNP | 75% |
| 1587 | s18 | REF | 70% |
| 1588 | s18 | SNP | 60% |
| 1589 | s18 | REF | 65% |
| 1590 | s18 | SNP | 70% |
| 1591 | s18 | SNP | 65% |
| 1592 | s18 | REF | 60% |
| 1593 | s18 | SNP | 65% |
| 1594 | s18 | REF | 60% |
| 1595 | s18 | REF | 60% |
| 1596 | s18 | SNP | 65% |
| 1597 | s18 | REF | 60% |
| 1598 | s18 | SNP | 70% |
| 1599 | s18 | REF | 65% |
| 1600 | s18 | SNP | 70% |
| 1601 | s18 | REF | 65% |
| 1602 | s18 | SNP | 65% |
| 1603 | s18 | REF | 60% |
| 1604 | s18 | SNP | 65% |
| 1605 | s18 | REF | 60% |
| 1606 | s18 | SNP | 65% |
| 1607 | s18 | REF | 60% |
| 1608 | s37 | SNP | 40% |
| 1609 | s37 | SNP | 35% |
| 1610 | s37 | SNP | 45% |
| 1611 | s19 | REF | 45% |
| 1612 | s19 | SNP | 45% |
| 1613 | s19 | SNP | 55% |
| 1614 | s19 | REF | 55% |
| 1615 | s19 | REF | 55% |
| 1616 | s19 | SNP | 55% |
| 1617 | s19 | SNP | 45% |
| 1618 | s19 | REF | 45% |
| 1619 | s19 | SNP | 55% |
| 1620 | s19 | REF | 55% |
| 1621 | s19 | SNP | 50% |
| 1622 | s19 | REF | 55% |
| 1623 | s19 | SNP | 55% |
| 1624 | s19 | REF | 55% |
| 1625 | s19 | SNP | 55% |
| 1626 | s19 | REF | 50% |
| 1627 | s19 | SNP | 50% |
| 1628 | s19 | SNP | 55% |
| 1629 | s19 | REF | 55% |
| 1630 | s19 | SNP | 50% |
| 1631 | s19 | REF | 50% |
| 1632 | s19 | REF | 55% |
| 1633 | s19 | REF | 60% |
| 1634 | s19 | REF | 50% |
| 1635 | s19 | SNP | 50% |
| 1636 | s19 | SNP | 55% |
| 1637 | s19 | REF | 55% |
| 1638 | s19 | SNP | 45% |
| 1639 | s19 | REF | 45% |
| 1640 | s19 | SNP | 55% |
| 1641 | s19 | REF | 55% |
| 1642 | s19 | SNP | 55% |
| 1643 | s19 | REF | 50% |
| 1644 | s19 | SNP | 50% |
| 1645 | s19 | REF | 55% |
| 1646 | s19 | SNP | 55% |
| 1647 | s19 | SNP | 50% |
| 1648 | s19 | SNP | 50% |
| 1649 | s19 | REF | 50% |
| 1650 | s19 | SNP | 45% |
| 1651 | s19 | REF | 45% |
| 1652 | s19 | REF | 50% |
| 1653 | s19 | SNP | 50% |
| 1654 | s19 | REF | 55% |
| 1655 | s19 | SNP | 50% |
| 1656 | s19 | REF | 50% |
| 1657 | s19 | SNP | 55% |
| 1658 | s19 | SNP | 45% |
| 1659 | s19 | REF | 45% |
| 1660 | s19 | SNP | 45% |
| 1661 | s20 | SNP | 70% |
| 1662 | s20 | REF | 65% |
| 1663 | s20 | REF | 65% |
| 1664 | s20 | SNP | 70% |
| 1665 | s20 | REF | 65% |
| 1666 | s20 | SNP | 70% |
| 1667 | s20 | SNP | 70% |
| 1668 | s20 | REF | 65% |
| 1669 | s20 | REF | 70% |
| 1670 | s20 | SNP | 75% |
| 1671 | s20 | REF | 65% |
| 1672 | s20 | SNP | 65% |
| 1673 | s20 | SNP | 70% |
| 1674 | s20 | REF | 65% |
| 1675 | s20 | REF | 65% |
| 1676 | s20 | SNP | 70% |
| 1677 | s20 | SNP | 75% |
| 1678 | s20 | REF | 70% |
| 1679 | s20 | SNP | 65% |
| 1680 | s20 | REF | 60% |
| 1681 | s20 | SNP | 65% |
| 1682 | s20 | REF | 60% |
| 1683 | s20 | SNP | 70% |
| 1684 | s20 | REF | 65% |
| 1685 | s20 | REF | 65% |
| 1686 | s20 | SNP | 70% |
| 1687 | s20 | SNP | 70% |
| 1688 | s20 | REF | 65% |
| 1689 | s20 | REF | 65% |
| 1690 | s20 | SNP | 70% |
| 1691 | s20 | SNP | 70% |
| 1692 | s20 | REF | 65% |
| 1693 | s20 | SNP | 75% |
| 1694 | s20 | REF | 70% |
| 1695 | s20 | SNP | 70% |
| 1696 | s20 | REF | 65% |
| 1697 | s20 | REF | 65% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1698 | s20 | SNP | 70% |
| 1699 | s20 | REF | 70% |
| 1700 | s20 | SNP | 75% |
| 1701 | s20 | REF | 65% |
| 1702 | s20 | SNP | 70% |
| 1703 | s20 | REF | 65% |
| 1704 | s20 | SNP | 70% |
| 1705 | s20 | REF | 65% |
| 1706 | s20 | SNP | 65% |
| 1707 | s20 | REF | 60% |
| 1708 | s20 | SNP | 65% |
| 1709 | s20 | REF | 60% |
| 1710 | s20 | REF | 65% |
| 1711 | s20 | SNP | 70% |
| 1712 | s20 | REF | 65% |
| 1713 | s20 | REF | 65% |
| 1714 | s20 | SNP | 70% |
| 1715 | s20 | REF | 60% |
| 1716 | s20 | SNP | 65% |
| 1717 | s21 | REF | 40% |
| 1718 | s21 | SNP | 45% |
| 1719 | s21 | REF | 60% |
| 1720 | s21 | SNP | 50% |
| 1721 | s21 | REF | 55% |
| 1722 | s21 | SNP | 60% |
| 1723 | s21 | REF | 45% |
| 1724 | s21 | SNP | 50% |
| 1725 | s21 | REF | 45% |
| 1726 | s21 | SNP | 50% |
| 1727 | s21 | SNP | 50% |
| 1728 | s21 | REF | 50% |
| 1729 | s21 | SNP | 55% |
| 1730 | s21 | REF | 50% |
| 1731 | s21 | SNP | 55% |
| 1732 | s21 | SNP | 55% |
| 1733 | s21 | REF | 50% |
| 1734 | s21 | SNP | 55% |
| 1735 | s21 | REF | 50% |
| 1736 | s21 | SNP | 55% |
| 1737 | s21 | REF | 50% |
| 1738 | s21 | SNP | 50% |
| 1739 | s21 | REF | 45% |
| 1740 | s21 | REF | 45% |
| 1741 | s21 | SNP | 50% |
| 1742 | s21 | REF | 45% |
| 1743 | s21 | SNP | 50% |
| 1744 | s21 | SNP | 50% |
| 1745 | s21 | SNP | 65% |
| 1746 | s21 | SNP | 60% |
| 1747 | s21 | REF | 55% |
| 1748 | s21 | SNP | 50% |
| 1749 | s21 | REF | 45% |
| 1750 | s21 | REF | 45% |
| 1751 | s21 | SNP | 50% |
| 1752 | s21 | SNP | 50% |
| 1753 | s21 | SNP | 65% |
| 1754 | s21 | REF | 60% |
| 1755 | s21 | REF | 45% |
| 1756 | s21 | SNP | 50% |
| 1757 | s21 | SNP | 50% |
| 1758 | s21 | REF | 45% |
| 1759 | s21 | REF | 45% |
| 1760 | s21 | REF | 45% |
| 1761 | s21 | SNP | 50% |
| 1762 | s21 | REF | 45% |
| 1763 | s21 | REF | 60% |
| 1764 | s21 | REF | 50% |
| 1765 | s21 | SNP | 55% |
| 1766 | s21 | SNP | 55% |
| 1767 | s21 | REF | 50% |
| 1768 | s21 | REF | 40% |
| 1769 | s21 | SNP | 45% |
| 1770 | s21 | SNP | 65% |
| 1771 | s21 | SNP | 50% |
| 1772 | s21 | REF | 45% |
| 1773 | s21 | SNP | 65% |
| 1774 | s21 | REF | 60% |
| 1775 | s21 | SNP | 45% |
| 1776 | s21 | REF | 40% |
| 1777 | s21 | SNP | 50% |
| 1778 | s21 | REF | 45% |
| 1779 | s21 | REF | 45% |
| 1780 | s21 | SNP | 50% |
| 1781 | s21 | REF | 45% |
| 1782 | s21 | SNP | 50% |
| 1783 | s22 | REF | 55% |
| 1784 | s22 | REF | 50% |
| 1785 | s22 | SNP | 45% |
| 1786 | s22 | SNP | 40% |
| 1787 | s22 | REF | 45% |
| 1788 | s22 | REF | 45% |
| 1789 | s22 | REF | 55% |
| 1790 | s22 | SNP | 50% |
| 1791 | s22 | SNP | 40% |
| 1792 | s22 | REF | 50% |
| 1793 | s22 | SNP | 50% |
| 1794 | s22 | SNP | 50% |
| 1795 | s22 | REF | 55% |
| 1796 | s22 | SNP | 45% |
| 1797 | s22 | REF | 50% |
| 1798 | s22 | REF | 45% |
| 1799 | s22 | SNP | 40% |
| 1800 | s22 | SNP | 50% |
| 1801 | s22 | REF | 55% |
| 1802 | s22 | SNP | 50% |
| 1803 | s22 | REF | 55% |
| 1804 | s22 | REF | 55% |
| 1805 | s22 | REF | 55% |
| 1806 | s22 | SNP | 50% |
| 1807 | s22 | REF | 55% |
| 1808 | s22 | SNP | 50% |
| 1809 | s22 | SNP | 50% |
| 1810 | s22 | REF | 55% |
| 1811 | s22 | REF | 45% |
| 1812 | s22 | SNP | 40% |
| 1813 | s22 | REF | 55% |
| 1814 | s22 | SNP | 50% |
| 1815 | s22 | REF | 50% |
| 1816 | s22 | SNP | 45% |
| 1817 | s22 | REF | 55% |
| 1818 | s22 | SNP | 50% |
| 1819 | s22 | REF | 55% |
| 1820 | s22 | SNP | 50% |
| 1821 | s22 | SNP | 50% |
| 1822 | s22 | REF | 55% |
| 1823 | s22 | SNP | 45% |
| 1824 | s22 | REF | 50% |
| 1825 | s22 | SNP | 40% |
| 1826 | s22 | REF | 45% |
| 1827 | s22 | SNP | 40% |
| 1828 | s22 | REF | 45% |
| 1829 | s22 | SNP | 45% |
| 1830 | s22 | SNP | 50% |
| 1831 | s22 | REF | 55% |
| 1832 | s22 | REF | 50% |
| 1833 | s22 | REF | 50% |
| 1834 | s22 | REF | 55% |
| 1835 | s22 | SNP | 50% |
| 1836 | s22 | REF | 50% |
| 1837 | s22 | REF | 45% |
| 1838 | s22 | SNP | 50% |
| 1839 | s22 | REF | 55% |
| 1840 | s22 | SNP | 45% |
| 1841 | s22 | SNP | 40% |
| 1842 | s22 | REF | 45% |
| 1843 | s22 | SNP | 50% |
| 1844 | s22 | REF | 55% |
| 1845 | s23 | SNP | 55% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1846 | s23 | SNP | 60% |
| 1847 | s23 | SNP | 50% |
| 1848 | s23 | REF | 55% |
| 1849 | s23 | SNP | 60% |
| 1850 | s23 | REF | 65% |
| 1851 | s23 | SNP | 45% |
| 1852 | s23 | REF | 50% |
| 1853 | s23 | SNP | 70% |
| 1854 | s23 | REF | 65% |
| 1855 | s23 | SNP | 60% |
| 1856 | s23 | REF | 60% |
| 1857 | s23 | SNP | 55% |
| 1858 | s23 | SNP | 55% |
| 1859 | s23 | REF | 50% |
| 1860 | s23 | SNP | 45% |
| 1861 | s23 | REF | 65% |
| 1862 | s23 | SNP | 60% |
| 1863 | s23 | REF | 65% |
| 1864 | s23 | SNP | 60% |
| 1865 | s23 | REF | 65% |
| 1866 | s23 | SNP | 60% |
| 1867 | s23 | SNP | 65% |
| 1868 | s23 | SNP | 60% |
| 1869 | s23 | REF | 65% |
| 1870 | s23 | SNP | 60% |
| 1871 | s23 | REF | 65% |
| 1872 | s23 | SNP | 55% |
| 1873 | s23 | SNP | 50% |
| 1874 | s23 | REF | 55% |
| 1875 | s23 | SNP | 60% |
| 1876 | s23 | REF | 65% |
| 1877 | s23 | SNP | 50% |
| 1878 | s23 | REF | 55% |
| 1879 | s23 | REF | 55% |
| 1880 | s23 | SNP | 50% |
| 1881 | s23 | SNP | 55% |
| 1882 | s23 | REF | 60% |
| 1883 | s23 | REF | 55% |
| 1884 | s23 | SNP | 50% |
| 1885 | s23 | REF | 60% |
| 1886 | s23 | SNP | 55% |
| 1887 | s23 | REF | 65% |
| 1888 | s23 | SNP | 60% |
| 1889 | s23 | REF | 65% |
| 1890 | s23 | SNP | 60% |
| 1891 | s23 | REF | 60% |
| 1892 | s23 | REF | 65% |
| 1893 | s23 | SNP | 60% |
| 1894 | s23 | SNP | 60% |
| 1895 | s23 | REF | 55% |
| 1896 | s23 | SNP | 55% |
| 1897 | s23 | SNP | 50% |
| 1898 | s39 | SNP | 75% |
| 1899 | s39 | SNP | 60% |
| 1900 | s39 | SNP | 70% |
| 1901 | s39 | SNP | 70% |
| 1902 | s39 | SNP | 70% |
| 1903 | s39 | SNP | 65% |
| 1904 | s39 | SNP | 70% |
| 1905 | s39 | SNP | 70% |
| 1906 | s39 | SNP | 70% |
| 1907 | s39 | SNP | 70% |
| 1908 | s39 | SNP | 75% |
| 1909 | s39 | SNP | 70% |
| 1910 | s39 | SNP | 75% |
| 1911 | s39 | SNP | 70% |
| 1912 | s39 | SNP | 70% |
| 1913 | s39 | SNP | 70% |
| 1914 | s39 | SNP | 70% |
| 1915 | s39 | SNP | 70% |
| 1916 | s39 | SNP | 70% |
| 1917 | s39 | SNP | 70% |
| 1918 | s39 | SNP | 70% |
| 1919 | s39 | SNP | 75% |
| 1920 | s39 | SNP | 70% |
| 1921 | s39 | SNP | 60% |
| 1922 | s39 | SNP | 70% |
| 1923 | s39 | SNP | 65% |
| 1924 | s39 | SNP | 70% |
| 1925 | s39 | SNP | 70% |
| 1926 | s39 | SNP | 70% |
| 1927 | s39 | SNP | 70% |
| 1928 | s38 | SNP | 35% |
| 1929 | s38 | SNP | 45% |
| 1930 | s38 | SNP | 45% |
| 1931 | s24 | REF | 60% |
| 1932 | s24 | SNP | 55% |
| 1933 | s24 | SNP | 55% |
| 1934 | s24 | SNP | 55% |
| 1935 | s24 | REF | 60% |
| 1936 | s24 | SNP | 55% |
| 1937 | s24 | REF | 65% |
| 1938 | s24 | SNP | 60% |
| 1939 | s24 | SNP | 55% |
| 1940 | s24 | REF | 60% |
| 1941 | s24 | SNP | 60% |
| 1942 | s24 | REF | 65% |
| 1943 | s24 | SNP | 60% |
| 1944 | s24 | SNP | 55% |
| 1945 | s24 | REF | 60% |
| 1946 | s24 | SNP | 60% |
| 1947 | s24 | SNP | 60% |
| 1948 | s24 | REF | 65% |
| 1949 | s24 | SNP | 60% |
| 1950 | s24 | SNP | 70% |
| 1951 | s24 | SNP | 70% |
| 1952 | s24 | SNP | 60% |
| 1953 | s24 | SNP | 60% |
| 1954 | s24 | SNP | 70% |
| 1955 | s24 | REF | 65% |
| 1956 | s24 | SNP | 60% |
| 1957 | s24 | REF | 65% |
| 1958 | s24 | SNP | 70% |
| 1959 | s24 | REF | 60% |
| 1960 | s24 | REF | 65% |
| 1961 | s24 | SNP | 60% |
| 1962 | s24 | SNP | 55% |
| 1963 | s24 | SNP | 55% |
| 1964 | s24 | SNP | 65% |
| 1965 | s24 | SNP | 60% |
| 1966 | s25 | SNP | 40% |
| 1967 | s25 | SNP | 60% |
| 1968 | s25 | REF | 65% |
| 1969 | s25 | SNP | 45% |
| 1970 | s25 | REF | 50% |
| 1971 | s25 | REF | 70% |
| 1972 | s25 | SNP | 50% |
| 1973 | s25 | REF | 55% |
| 1974 | s25 | REF | 45% |
| 1975 | s25 | REF | 50% |
| 1976 | s25 | SNP | 45% |
| 1977 | s25 | SNP | 45% |
| 1978 | s25 | REF | 55% |
| 1979 | s25 | SNP | 50% |
| 1980 | s25 | SNP | 65% |
| 1981 | s25 | SNP | 65% |
| 1982 | s25 | REF | 70% |
| 1983 | s25 | SNP | 50% |
| 1984 | s25 | REF | 55% |
| 1985 | s25 | SNP | 55% |
| 1986 | s25 | REF | 60% |
| 1987 | s25 | REF | 50% |
| 1988 | s25 | SNP | 45% |
| 1989 | s25 | REF | 60% |
| 1990 | s25 | SNP | 55% |
| 1991 | s25 | SNP | 60% |
| 1992 | s25 | REF | 65% |
| 1993 | s25 | SNP | 60% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 1994 | s25 | REF | 65% |
| 1995 | s25 | SNP | 50% |
| 1996 | s25 | REF | 55% |
| 1997 | s25 | SNP | 45% |
| 1998 | s25 | REF | 50% |
| 1999 | s25 | SNP | 70% |
| 2000 | s25 | REF | 75% |
| 2001 | s25 | SNP | 45% |
| 2002 | s25 | REF | 50% |
| 2003 | s25 | REF | 55% |
| 2004 | s25 | SNP | 50% |
| 2005 | s25 | REF | 65% |
| 2006 | s25 | SNP | 60% |
| 2007 | s25 | SNP | 55% |
| 2008 | s25 | REF | 60% |
| 2009 | s25 | REF | 70% |
| 2010 | s25 | SNP | 60% |
| 2011 | s25 | REF | 65% |
| 2012 | s25 | SNP | 65% |
| 2013 | s25 | SNP | 65% |
| 2014 | s25 | REF | 70% |
| 2015 | s25 | REF | 50% |
| 2016 | s25 | REF | 55% |
| 2017 | s25 | SNP | 50% |
| 2018 | s25 | REF | 50% |
| 2019 | s25 | SNP | 45% |
| 2020 | s25 | REF | 60% |
| 2021 | s25 | SNP | 55% |
| 2022 | s26 | SNP | 35% |
| 2023 | s26 | SNP | 35% |
| 2024 | s26 | REF | 35% |
| 2025 | s26 | SNP | 35% |
| 2026 | s26 | REF | 35% |
| 2027 | s26 | SNP | 35% |
| 2028 | s26 | REF | 35% |
| 2029 | s26 | REF | 35% |
| 2030 | s26 | SNP | 40% |
| 2031 | s26 | REF | 40% |
| 2032 | s26 | REF | 35% |
| 2033 | s26 | REF | 35% |
| 2034 | s26 | REF | 35% |
| 2035 | s26 | REF | 35% |
| 2036 | s26 | REF | 35% |
| 2037 | s26 | REF | 40% |
| 2038 | s26 | SNP | 40% |
| 2039 | s26 | REF | 40% |
| 2040 | s26 | REF | 35% |
| 2041 | s26 | SNP | 40% |
| 2042 | s26 | REF | 40% |
| 2043 | s26 | REF | 40% |
| 2044 | s26 | SNP | 40% |
| 2045 | s26 | REF | 40% |
| 2046 | s26 | REF | 35% |
| 2047 | s26 | REF | 40% |
| 2048 | s26 | SNP | 40% |
| 2049 | s26 | REF | 40% |
| 2050 | s26 | SNP | 35% |
| 2051 | s26 | REF | 35% |
| 2052 | s26 | SNP | 35% |
| 2053 | s26 | REF | 35% |
| 2054 | s26 | REF | 35% |
| 2055 | s26 | SNP | 35% |
| 2056 | s26 | REF | 35% |
| 2057 | s26 | SNP | 35% |
| 2058 | s26 | REF | 35% |
| 2059 | s73 | SNP | 35% |
| 2060 | s73 | SNP | 40% |
| 2061 | s73 | SNP | 40% |
| 2062 | s6 | SNP | 35% |
| 2063 | s27 | REF | 75% |
| 2064 | s27 | SNP | 80% |
| 2065 | s27 | REF | 75% |
| 2066 | s27 | SNP | 80% |
| 2067 | s27 | REF | 75% |
| 2068 | s27 | SNP | 80% |
| 2069 | s27 | REF | 75% |
| 2070 | s27 | SNP | 80% |
| 2071 | s27 | REF | 80% |
| 2072 | s27 | SNP | 85% |
| 2073 | s27 | SNP | 85% |
| 2074 | s27 | REF | 80% |
| 2075 | s27 | SNP | 85% |
| 2076 | s27 | REF | 80% |
| 2077 | s27 | REF | 80% |
| 2078 | s27 | REF | 80% |
| 2079 | s27 | SNP | 85% |
| 2080 | s27 | SNP | 85% |
| 2081 | s27 | REF | 80% |
| 2082 | s27 | SNP | 80% |
| 2083 | s27 | SNP | 80% |
| 2084 | s27 | REF | 75% |
| 2085 | s27 | REF | 80% |
| 2086 | s27 | SNP | 85% |
| 2087 | s27 | REF | 75% |
| 2088 | s27 | SNP | 80% |
| 2089 | s27 | REF | 80% |
| 2090 | s27 | SNP | 85% |
| 2091 | s27 | SNP | 80% |
| 2092 | s27 | SNP | 85% |
| 2093 | s27 | REF | 80% |
| 2094 | s27 | SNP | 80% |
| 2095 | s27 | REF | 75% |
| 2096 | s27 | REF | 80% |
| 2097 | s27 | SNP | 85% |
| 2098 | s27 | SNP | 85% |
| 2099 | s27 | REF | 80% |
| 2100 | s27 | SNP | 85% |
| 2101 | s27 | REF | 80% |
| 2102 | s27 | SNP | 85% |
| 2103 | s27 | REF | 80% |
| 2104 | s27 | REF | 75% |
| 2105 | s27 | SNP | 80% |
| 2106 | s27 | REF | 75% |
| 2107 | s27 | SNP | 80% |
| 2108 | s27 | REF | 75% |
| 2109 | s27 | SNP | 85% |
| 2110 | s27 | REF | 80% |
| 2111 | s27 | REF | 75% |
| 2112 | s4 | SNP | 40% |
| 2113 | s4 | SNP | 45% |
| 2114 | s4 | SNP | 50% |
| 2115 | s4 | SNP | 50% |
| 2116 | s4 | SNP | 55% |
| 2117 | s4 | SNP | 40% |
| 2118 | s4 | SNP | 35% |
| 2119 | s4 | SNP | 45% |
| 2120 | s4 | SNP | 50% |
| 2121 | s4 | SNP | 55% |
| 2122 | s4 | SNP | 50% |
| 2123 | s28 | SNP | 60% |
| 2124 | s28 | REF | 65% |
| 2125 | s28 | REF | 70% |
| 2126 | s28 | SNP | 65% |
| 2127 | s28 | SNP | 60% |
| 2128 | s28 | REF | 65% |
| 2129 | s28 | SNP | 65% |
| 2130 | s28 | REF | 65% |
| 2131 | s28 | SNP | 65% |
| 2132 | s28 | REF | 70% |
| 2133 | s28 | SNP | 65% |
| 2134 | s28 | REF | 70% |
| 2135 | s28 | REF | 70% |
| 2136 | s28 | SNP | 65% |
| 2137 | s28 | REF | 70% |
| 2138 | s28 | SNP | 65% |
| 2139 | s28 | SNP | 65% |
| 2140 | s28 | REF | 70% |
| 2141 | s28 | SNP | 65% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2142 | s28 | REF | 70% |
| 2143 | s28 | SNP | 65% |
| 2144 | s28 | SNP | 65% |
| 2145 | s28 | SNP | 65% |
| 2146 | s28 | REF | 70% |
| 2147 | s28 | SNP | 65% |
| 2148 | s28 | SNP | 65% |
| 2149 | s28 | SNP | 65% |
| 2150 | s28 | REF | 70% |
| 2151 | s28 | REF | 70% |
| 2152 | s28 | SNP | 65% |
| 2153 | s28 | SNP | 65% |
| 2154 | s28 | REF | 70% |
| 2155 | s28 | SNP | 70% |
| 2156 | s28 | SNP | 65% |
| 2157 | s28 | SNP | 65% |
| 2158 | s28 | REF | 70% |
| 2159 | s28 | REF | 70% |
| 2160 | s28 | SNP | 65% |
| 2161 | s28 | REF | 70% |
| 2162 | s28 | REF | 70% |
| 2163 | s28 | SNP | 65% |
| 2164 | s28 | REF | 70% |
| 2165 | s28 | REF | 65% |
| 2166 | s28 | SNP | 60% |
| 2167 | s28 | REF | 65% |
| 2168 | s28 | SNP | 65% |
| 2169 | s28 | REF | 70% |
| 2170 | s28 | REF | 70% |
| 2171 | s28 | SNP | 65% |
| 2172 | s28 | REF | 65% |
| 2173 | s28 | SNP | 60% |
| 2174 | s28 | SNP | 60% |
| 2175 | s28 | REF | 65% |
| 2176 | s28 | SNP | 60% |
| 2177 | s28 | SNP | 65% |
| 2178 | s28 | REF | 70% |
| 2179 | s28 | REF | 70% |
| 2180 | s28 | SNP | 65% |
| 2181 | s3 | SNP | 40% |
| 2182 | s3 | SNP | 45% |
| 2183 | s3 | SNP | 50% |
| 2184 | s3 | SNP | 50% |
| 2185 | s3 | SNP | 55% |
| 2186 | s3 | SNP | 40% |
| 2187 | s3 | SNP | 35% |
| 2188 | s3 | SNP | 45% |
| 2189 | s3 | SNP | 55% |
| 2190 | s3 | SNP | 50% |
| 2191 | s3 | SNP | 55% |
| 2192 | s3 | SNP | 50% |
| 2193 | s3 | SNP | 55% |
| 2194 | s30 | SNP | 35% |
| 2195 | s30 | SNP | 50% |
| 2196 | s30 | REF | 45% |
| 2197 | s30 | REF | 45% |
| 2198 | s30 | SNP | 50% |
| 2199 | s30 | SNP | 65% |
| 2200 | s30 | REF | 60% |
| 2201 | s30 | REF | 45% |
| 2202 | s30 | REF | 35% |
| 2203 | s30 | SNP | 40% |
| 2204 | s30 | REF | 60% |
| 2205 | s30 | REF | 35% |
| 2206 | s30 | SNP | 40% |
| 2207 | s30 | SNP | 50% |
| 2208 | s30 | REF | 45% |
| 2209 | s30 | SNP | 40% |
| 2210 | s30 | REF | 35% |
| 2211 | s30 | SNP | 45% |
| 2212 | s30 | REF | 40% |
| 2213 | s30 | SNP | 35% |
| 2214 | s30 | SNP | 45% |
| 2215 | s30 | REF | 40% |
| 2216 | s30 | SNP | 50% |
| 2217 | s30 | REF | 45% |
| 2218 | s30 | SNP | 65% |
| 2219 | s30 | REF | 60% |
| 2220 | s30 | SNP | 35% |
| 2221 | s30 | SNP | 60% |
| 2222 | s30 | REF | 55% |
| 2223 | s30 | REF | 50% |
| 2224 | s30 | SNP | 55% |
| 2225 | s30 | REF | 50% |
| 2226 | s30 | REF | 35% |
| 2227 | s30 | SNP | 40% |
| 2228 | s30 | REF | 35% |
| 2229 | s30 | SNP | 55% |
| 2230 | s30 | REF | 50% |
| 2231 | s30 | SNP | 65% |
| 2232 | s30 | REF | 40% |
| 2233 | s30 | SNP | 45% |
| 2234 | s30 | REF | 40% |
| 2235 | s30 | SNP | 45% |
| 2236 | s30 | REF | 60% |
| 2237 | s30 | SNP | 35% |
| 2238 | s30 | SNP | 55% |
| 2239 | s30 | REF | 50% |
| 2240 | s30 | SNP | 65% |
| 2241 | s30 | REF | 55% |
| 2242 | s30 | SNP | 60% |
| 2243 | s30 | REF | 50% |
| 2244 | s30 | SNP | 55% |
| 2245 | s31 | SNP | 75% |
| 2246 | s31 | REF | 75% |
| 2247 | s31 | SNP | 55% |
| 2248 | s31 | REF | 50% |
| 2249 | s31 | REF | 70% |
| 2250 | s31 | REF | 70% |
| 2251 | s31 | REF | 70% |
| 2252 | s31 | SNP | 55% |
| 2253 | s31 | REF | 50% |
| 2254 | s31 | SNP | 55% |
| 2255 | s31 | REF | 70% |
| 2256 | s31 | SNP | 60% |
| 2257 | s31 | REF | 55% |
| 2258 | s31 | SNP | 70% |
| 2259 | s31 | REF | 65% |
| 2260 | s31 | SNP | 70% |
| 2261 | s31 | REF | 65% |
| 2262 | s31 | REF | 65% |
| 2263 | s31 | SNP | 75% |
| 2264 | s31 | REF | 70% |
| 2265 | s31 | SNP | 65% |
| 2266 | s31 | REF | 60% |
| 2267 | s31 | SNP | 75% |
| 2268 | s31 | REF | 70% |
| 2269 | s31 | REF | 55% |
| 2270 | s31 | SNP | 70% |
| 2271 | s31 | REF | 65% |
| 2272 | s31 | SNP | 55% |
| 2273 | s31 | REF | 50% |
| 2274 | s31 | SNP | 70% |
| 2275 | s31 | REF | 65% |
| 2276 | s31 | REF | 65% |
| 2277 | s31 | SNP | 70% |
| 2278 | s31 | REF | 70% |
| 2279 | s31 | REF | 70% |
| 2280 | s31 | REF | 70% |
| 2281 | s31 | SNP | 55% |
| 2282 | s31 | SNP | 75% |
| 2283 | s31 | REF | 50% |
| 2284 | s32 | SNP | 60% |
| 2285 | s32 | SNP | 70% |
| 2286 | s32 | SNP | 60% |
| 2287 | s32 | REF | 65% |
| 2288 | s32 | SNP | 70% |
| 2289 | s32 | REF | 70% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2290 | s32 | SNP | 65% |
| 2291 | s32 | SNP | 70% |
| 2292 | s32 | SNP | 70% |
| 2293 | s32 | REF | 70% |
| 2294 | s32 | SNP | 65% |
| 2295 | s32 | SNP | 60% |
| 2296 | s32 | REF | 65% |
| 2297 | s32 | REF | 75% |
| 2298 | s32 | SNP | 70% |
| 2299 | s32 | SNP | 70% |
| 2300 | s32 | REF | 75% |
| 2301 | s32 | SNP | 65% |
| 2302 | s32 | REF | 70% |
| 2303 | s32 | REF | 65% |
| 2304 | s32 | SNP | 70% |
| 2305 | s32 | REF | 70% |
| 2306 | s32 | SNP | 65% |
| 2307 | s32 | SNP | 70% |
| 2308 | s32 | REF | 75% |
| 2309 | s32 | SNP | 65% |
| 2310 | s32 | SNP | 65% |
| 2311 | s32 | REF | 70% |
| 2312 | s32 | REF | 65% |
| 2313 | s32 | REF | 70% |
| 2314 | s32 | SNP | 65% |
| 2315 | s32 | SNP | 65% |
| 2316 | s32 | SNP | 70% |
| 2317 | s32 | REF | 75% |
| 2318 | s32 | REF | 70% |
| 2319 | s32 | SNP | 70% |
| 2320 | s32 | REF | 75% |
| 2321 | s32 | REF | 70% |
| 2322 | s32 | SNP | 65% |
| 2323 | s32 | REF | 70% |
| 2324 | s32 | SNP | 65% |
| 2325 | s32 | SNP | 60% |
| 2326 | s32 | REF | 70% |
| 2327 | s32 | SNP | 65% |
| 2328 | s32 | SNP | 60% |
| 2329 | s32 | REF | 70% |
| 2330 | s32 | SNP | 65% |
| 2331 | s32 | REF | 65% |
| 2332 | s32 | SNP | 60% |
| 2333 | s74 | SNP | 60% |
| 2334 | s74 | SNP | 60% |
| 2335 | s74 | SNP | 65% |
| 2336 | s74 | SNP | 65% |
| 2337 | s74 | SNP | 70% |
| 2338 | s74 | SNP | 60% |
| 2339 | s74 | SNP | 60% |
| 2340 | s33 | REF | 60% |
| 2341 | s33 | SNP | 65% |
| 2342 | s33 | SNP | 40% |
| 2343 | s33 | SNP | 65% |
| 2344 | s33 | REF | 60% |
| 2345 | s33 | REF | 40% |
| 2346 | s33 | SNP | 45% |
| 2347 | s33 | REF | 35% |
| 2348 | s33 | REF | 45% |
| 2349 | s33 | SNP | 50% |
| 2350 | s33 | SNP | 50% |
| 2351 | s33 | REF | 55% |
| 2352 | s33 | SNP | 60% |
| 2353 | s33 | REF | 45% |
| 2354 | s33 | REF | 50% |
| 2355 | s33 | SNP | 55% |
| 2356 | s33 | SNP | 45% |
| 2357 | s33 | REF | 60% |
| 2358 | s33 | SNP | 65% |
| 2359 | s33 | SNP | 65% |
| 2360 | s33 | REF | 60% |
| 2361 | s33 | SNP | 60% |
| 2362 | s33 | REF | 55% |
| 2363 | s33 | SNP | 55% |
| 2364 | s33 | REF | 50% |
| 2365 | s33 | REF | 55% |
| 2366 | s33 | SNP | 60% |
| 2367 | s33 | REF | 55% |
| 2368 | s33 | SNP | 60% |
| 2369 | s33 | SNP | 60% |
| 2370 | s33 | REF | 45% |
| 2371 | s33 | SNP | 50% |
| 2372 | s33 | SNP | 50% |
| 2373 | s33 | REF | 45% |
| 2374 | s33 | REF | 50% |
| 2375 | s33 | SNP | 55% |
| 2376 | s33 | SNP | 60% |
| 2377 | s33 | REF | 55% |
| 2378 | s33 | REF | 55% |
| 2379 | s33 | SNP | 60% |
| 2380 | s33 | REF | 40% |
| 2381 | s33 | REF | 55% |
| 2382 | s33 | SNP | 60% |
| 2383 | s33 | SNP | 55% |
| 2384 | s33 | SNP | 55% |
| 2385 | s33 | REF | 50% |
| 2386 | s34 | SNP | 35% |
| 2387 | s34 | REF | 45% |
| 2388 | s34 | SNP | 40% |
| 2389 | s34 | SNP | 45% |
| 2390 | s34 | REF | 50% |
| 2391 | s34 | SNP | 40% |
| 2392 | s34 | REF | 45% |
| 2393 | s34 | SNP | 45% |
| 2394 | s34 | REF | 50% |
| 2395 | s34 | SNP | 40% |
| 2396 | s34 | REF | 45% |
| 2397 | s34 | REF | 45% |
| 2398 | s34 | SNP | 40% |
| 2399 | s34 | REF | 40% |
| 2400 | s34 | SNP | 35% |
| 2401 | s34 | SNP | 35% |
| 2402 | s34 | SNP | 45% |
| 2403 | s34 | REF | 50% |
| 2404 | s34 | SNP | 45% |
| 2405 | s34 | REF | 50% |
| 2406 | s34 | REF | 55% |
| 2407 | s34 | SNP | 50% |
| 2408 | s34 | SNP | 40% |
| 2409 | s34 | SNP | 40% |
| 2410 | s34 | SNP | 45% |
| 2411 | s34 | SNP | 45% |
| 2412 | s34 | REF | 50% |
| 2413 | s34 | REF | 55% |
| 2414 | s34 | REF | 50% |
| 2415 | s34 | REF | 50% |
| 2416 | s34 | SNP | 45% |
| 2417 | s34 | SNP | 50% |
| 2418 | s34 | SNP | 35% |
| 2419 | s34 | SNP | 35% |
| 2420 | s34 | REF | 40% |
| 2421 | s34 | SNP | 35% |
| 2422 | s34 | SNP | 45% |
| 2423 | s34 | REF | 50% |
| 2424 | s34 | REF | 50% |
| 2425 | s34 | SNP | 45% |
| 2426 | s34 | REF | 45% |
| 2427 | s34 | SNP | 40% |
| 2428 | s34 | REF | 50% |
| 2429 | s34 | SNP | 45% |
| 2430 | s34 | SNP | 45% |
| 2431 | s34 | SNP | 35% |
| 2432 | s35 | SNP | 70% |
| 2433 | s35 | REF | 80% |
| 2434 | s35 | SNP | 75% |
| 2435 | s35 | REF | 70% |
| 2436 | s35 | SNP | 65% |
| 2437 | s35 | SNP | 75% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2438 | s35 | REF | 80% |
| 2439 | s35 | REF | 90% |
| 2440 | s35 | SNP | 75% |
| 2441 | s35 | REF | 80% |
| 2442 | s35 | SNP | 80% |
| 2443 | s35 | REF | 85% |
| 2444 | s35 | SNP | 80% |
| 2445 | s35 | REF | 85% |
| 2446 | s35 | SNP | 70% |
| 2447 | s35 | REF | 75% |
| 2448 | s35 | REF | 85% |
| 2449 | s35 | SNP | 80% |
| 2450 | s35 | SNP | 70% |
| 2451 | s35 | REF | 75% |
| 2452 | s35 | REF | 85% |
| 2453 | s35 | REF | 75% |
| 2454 | s35 | SNP | 70% |
| 2455 | s35 | SNP | 80% |
| 2456 | s35 | REF | 75% |
| 2457 | s35 | SNP | 70% |
| 2458 | s35 | SNP | 70% |
| 2459 | s35 | REF | 75% |
| 2460 | s35 | REF | 75% |
| 2461 | s35 | SNP | 70% |
| 2462 | s35 | REF | 75% |
| 2463 | s35 | SNP | 70% |
| 2464 | s35 | REF | 75% |
| 2465 | s35 | SNP | 70% |
| 2466 | s35 | REF | 75% |
| 2467 | s35 | SNP | 70% |
| 2468 | s35 | REF | 75% |
| 2469 | s35 | SNP | 65% |
| 2470 | s35 | SNP | 85% |
| 2471 | s35 | REF | 85% |
| 2472 | s35 | REF | 70% |
| 2473 | s35 | SNP | 80% |
| 2474 | s36 | SNP | 60% |
| 2475 | s36 | SNP | 65% |
| 2476 | s36 | SNP | 70% |
| 2477 | s36 | SNP | 60% |
| 2478 | s36 | SNP | 65% |
| 2479 | s36 | SNP | 70% |
| 2480 | s36 | SNP | 70% |
| 2481 | s36 | SNP | 65% |
| 2482 | s36 | REF | 70% |
| 2483 | s36 | SNP | 65% |
| 2484 | s36 | REF | 70% |
| 2485 | s36 | SNP | 60% |
| 2486 | s36 | SNP | 60% |
| 2487 | s36 | SNP | 60% |
| 2488 | s36 | REF | 65% |
| 2489 | s36 | SNP | 60% |
| 2490 | s36 | SNP | 70% |
| 2491 | s36 | SNP | 65% |
| 2492 | s36 | REF | 70% |
| 2493 | s36 | SNP | 65% |
| 2494 | s36 | SNP | 70% |
| 2495 | s36 | REF | 65% |
| 2496 | s36 | REF | 70% |
| 2497 | s36 | REF | 70% |
| 2498 | s36 | SNP | 65% |
| 2499 | s36 | SNP | 60% |
| 2500 | s36 | SNP | 60% |
| 2501 | s36 | REF | 65% |
| 2502 | s36 | SNP | 55% |
| 2503 | s36 | SNP | 60% |
| 2504 | s36 | SNP | 65% |
| 2505 | s36 | REF | 70% |
| 2506 | s36 | SNP | 60% |
| 2507 | s36 | SNP | 55% |
| 2508 | s7 | SNP | 40% |
| 2509 | s7 | SNP | 45% |
| 2510 | s7 | SNP | 50% |
| 2511 | s7 | SNP | 45% |
| 2512 | s7 | SNP | 35% |
| 2513 | s7 | SNP | 50% |
| 2514 | s7 | SNP | 40% |
| 2515 | s29 | SNP | 65% |
| 2516 | s29 | SNP | 65% |
| 2517 | s29 | SNP | 65% |
| 2518 | s29 | SNP | 65% |
| 2519 | s29 | SNP | 65% |
| 2520 | s29 | SNP | 75% |
| 2521 | s29 | SNP | 70% |
| 2522 | s29 | SNP | 65% |
| 2523 | s29 | SNP | 65% |
| 2524 | s29 | SNP | 75% |
| 2525 | s29 | SNP | 75% |
| 2526 | s29 | SNP | 75% |
| 2527 | s29 | SNP | 65% |
| 2528 | s29 | SNP | 75% |
| 2529 | s29 | REF | 65% |
| 2530 | s29 | SNP | 75% |
| 2531 | s29 | SNP | 75% |
| 2532 | s40 | SNP | 35% |
| 2533 | s40 | SNP | 35% |
| 2534 | s40 | SNP | 35% |
| 2535 | s40 | REF | 35% |
| 2536 | s40 | REF | 35% |
| 2537 | s40 | SNP | 35% |
| 2538 | s40 | SNP | 40% |
| 2539 | s40 | REF | 40% |
| 2540 | s40 | REF | 35% |
| 2541 | s40 | REF | 35% |
| 2542 | s40 | SNP | 35% |
| 2543 | s40 | SNP | 40% |
| 2544 | s40 | REF | 40% |
| 2545 | s40 | SNP | 40% |
| 2546 | s40 | SNP | 50% |
| 2547 | s40 | SNP | 45% |
| 2548 | s40 | REF | 45% |
| 2549 | s41 | SNP | 65% |
| 2550 | s41 | REF | 70% |
| 2551 | s41 | REF | 60% |
| 2552 | s41 | SNP | 55% |
| 2553 | s41 | REF | 80% |
| 2554 | s41 | SNP | 75% |
| 2555 | s41 | SNP | 70% |
| 2556 | s41 | REF | 75% |
| 2557 | s41 | SNP | 75% |
| 2558 | s41 | REF | 65% |
| 2559 | s41 | SNP | 60% |
| 2560 | s41 | REF | 80% |
| 2561 | s41 | SNP | 75% |
| 2562 | s41 | REF | 70% |
| 2563 | s41 | SNP | 65% |
| 2564 | s41 | REF | 70% |
| 2565 | s41 | SNP | 65% |
| 2566 | s41 | REF | 70% |
| 2567 | s41 | SNP | 65% |
| 2568 | s41 | REF | 70% |
| 2569 | s41 | SNP | 65% |
| 2570 | s41 | REF | 65% |
| 2571 | s41 | SNP | 60% |
| 2572 | s41 | REF | 65% |
| 2573 | s41 | REF | 80% |
| 2574 | s41 | SNP | 75% |
| 2575 | s41 | REF | 80% |
| 2576 | s41 | REF | 80% |
| 2577 | s41 | SNP | 75% |
| 2578 | s41 | SNP | 60% |
| 2579 | s41 | SNP | 75% |
| 2580 | s41 | REF | 80% |
| 2581 | s41 | SNP | 75% |
| 2582 | s41 | REF | 80% |
| 2583 | s41 | REF | 80% |
| 2584 | s41 | SNP | 75% |
| 2585 | s41 | REF | 80% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2586 | s41 | SNP | 75% |
| 2587 | s41 | SNP | 75% |
| 2588 | s41 | SNP | 60% |
| 2589 | s41 | REF | 65% |
| 2590 | s41 | REF | 80% |
| 2591 | s41 | REF | 80% |
| 2592 | s41 | SNP | 75% |
| 2593 | s41 | SNP | 65% |
| 2594 | s41 | REF | 70% |
| 2595 | s41 | SNP | 65% |
| 2596 | s41 | REF | 70% |
| 2597 | s41 | REF | 70% |
| 2598 | s41 | SNP | 65% |
| 2599 | s41 | SNP | 75% |
| 2600 | s41 | REF | 80% |
| 2601 | s41 | SNP | 60% |
| 2602 | s41 | REF | 65% |
| 2603 | s41 | REF | 80% |
| 2604 | s41 | SNP | 75% |
| 2605 | s41 | SNP | 75% |
| 2606 | s41 | REF | 80% |
| 2607 | s42 | REF | 75% |
| 2608 | s42 | REF | 85% |
| 2609 | s42 | REF | 60% |
| 2610 | s42 | SNP | 55% |
| 2611 | s42 | SNP | 55% |
| 2612 | s42 | SNP | 60% |
| 2613 | s42 | REF | 80% |
| 2614 | s42 | SNP | 75% |
| 2615 | s42 | REF | 75% |
| 2616 | s42 | SNP | 70% |
| 2617 | s42 | REF | 60% |
| 2618 | s42 | SNP | 55% |
| 2619 | s42 | REF | 55% |
| 2620 | s42 | REF | 85% |
| 2621 | s42 | REF | 85% |
| 2622 | s42 | SNP | 80% |
| 2623 | s42 | REF | 80% |
| 2624 | s42 | REF | 60% |
| 2625 | s42 | SNP | 80% |
| 2626 | s42 | REF | 85% |
| 2627 | s42 | REF | 65% |
| 2628 | s42 | SNP | 60% |
| 2629 | s42 | SNP | 80% |
| 2630 | s42 | SNP | 65% |
| 2631 | s42 | SNP | 80% |
| 2632 | s42 | REF | 85% |
| 2633 | s42 | REF | 60% |
| 2634 | s42 | SNP | 55% |
| 2635 | s42 | SNP | 55% |
| 2636 | s42 | REF | 60% |
| 2637 | s42 | SNP | 65% |
| 2638 | s42 | REF | 70% |
| 2639 | s42 | REF | 60% |
| 2640 | s42 | REF | 65% |
| 2641 | s42 | SNP | 70% |
| 2642 | s42 | REF | 60% |
| 2643 | s42 | SNP | 60% |
| 2644 | s42 | REF | 65% |
| 2645 | s42 | SNP | 75% |
| 2646 | s42 | REF | 80% |
| 2647 | s42 | SNP | 60% |
| 2648 | s42 | REF | 65% |
| 2649 | s42 | SNP | 80% |
| 2650 | s42 | SNP | 65% |
| 2651 | s42 | REF | 70% |
| 2652 | s42 | SNP | 65% |
| 2653 | s42 | REF | 85% |
| 2654 | s42 | REF | 65% |
| 2655 | s42 | SNP | 60% |
| 2656 | s42 | REF | 65% |
| 2657 | s42 | SNP | 60% |
| 2658 | s42 | REF | 85% |
| 2659 | s42 | SNP | 80% |
| 2660 | s42 | SNP | 75% |
| 2661 | s42 | SNP | 60% |
| 2662 | s42 | SNP | 60% |
| 2663 | s42 | REF | 65% |
| 2664 | s75 | SNP | 45% |
| 2665 | s75 | SNP | 35% |
| 2666 | s75 | SNP | 45% |
| 2667 | s75 | SNP | 35% |
| 2668 | s75 | REF | 40% |
| 2669 | s75 | REF | 35% |
| 2670 | s75 | SNP | 40% |
| 2671 | s75 | SNP | 45% |
| 2672 | s75 | SNP | 35% |
| 2673 | s75 | SNP | 45% |
| 2674 | s75 | SNP | 45% |
| 2675 | s75 | SNP | 35% |
| 2676 | s75 | SNP | 45% |
| 2677 | s43 | SNP | 50% |
| 2678 | s43 | SNP | 65% |
| 2679 | s43 | REF | 60% |
| 2680 | s43 | REF | 65% |
| 2681 | s43 | SNP | 70% |
| 2682 | s43 | SNP | 75% |
| 2683 | s43 | REF | 70% |
| 2684 | s43 | SNP | 75% |
| 2685 | s43 | REF | 55% |
| 2686 | s43 | SNP | 70% |
| 2687 | s43 | REF | 65% |
| 2688 | s43 | SNP | 75% |
| 2689 | s43 | REF | 70% |
| 2690 | s43 | REF | 70% |
| 2691 | s43 | SNP | 70% |
| 2692 | s43 | SNP | 75% |
| 2693 | s43 | SNP | 75% |
| 2694 | s43 | REF | 70% |
| 2695 | s43 | SNP | 65% |
| 2696 | s43 | REF | 60% |
| 2697 | s43 | SNP | 65% |
| 2698 | s43 | REF | 70% |
| 2699 | s43 | SNP | 65% |
| 2700 | s43 | REF | 60% |
| 2701 | s43 | SNP | 65% |
| 2702 | s43 | REF | 70% |
| 2703 | s43 | SNP | 75% |
| 2704 | s43 | SNP | 65% |
| 2705 | s43 | SNP | 75% |
| 2706 | s43 | REF | 70% |
| 2707 | s43 | SNP | 70% |
| 2708 | s43 | REF | 70% |
| 2709 | s43 | SNP | 75% |
| 2710 | s43 | SNP | 65% |
| 2711 | s43 | REF | 60% |
| 2712 | s43 | REF | 60% |
| 2713 | s43 | REF | 70% |
| 2714 | s43 | SNP | 75% |
| 2715 | s43 | SNP | 60% |
| 2716 | s43 | REF | 60% |
| 2717 | s43 | SNP | 80% |
| 2718 | s43 | SNP | 65% |
| 2719 | s43 | SNP | 65% |
| 2720 | s43 | SNP | 65% |
| 2721 | s43 | SNP | 80% |
| 2722 | s43 | REF | 75% |
| 2723 | s43 | REF | 65% |
| 2724 | s43 | SNP | 60% |
| 2725 | s43 | REF | 55% |
| 2726 | s43 | SNP | 75% |
| 2727 | s43 | REF | 70% |
| 2728 | s43 | SNP | 65% |
| 2729 | s43 | REF | 60% |
| 2730 | s43 | REF | 70% |
| 2731 | s43 | SNP | 75% |
| 2732 | s43 | SNP | 65% |
| 2733 | s43 | SNP | 75% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2734 | s43 | REF | 70% |
| 2735 | s43 | REF | 70% |
| 2736 | s43 | SNP | 75% |
| 2737 | s44 | SNP | 35% |
| 2738 | s44 | SNP | 35% |
| 2739 | s44 | REF | 35% |
| 2740 | s44 | SNP | 40% |
| 2741 | s44 | REF | 35% |
| 2742 | s44 | SNP | 45% |
| 2743 | s44 | REF | 40% |
| 2744 | s44 | SNP | 45% |
| 2745 | s44 | REF | 35% |
| 2746 | s44 | REF | 45% |
| 2747 | s44 | SNP | 45% |
| 2748 | s44 | REF | 45% |
| 2749 | s44 | REF | 35% |
| 2750 | s44 | REF | 40% |
| 2751 | s44 | REF | 40% |
| 2752 | s44 | REF | 60% |
| 2753 | s44 | REF | 35% |
| 2754 | s44 | REF | 40% |
| 2755 | s44 | REF | 45% |
| 2756 | s44 | SNP | 45% |
| 2757 | s44 | REF | 45% |
| 2758 | s44 | SNP | 50% |
| 2759 | s2 | SNP | 40% |
| 2760 | s2 | SNP | 45% |
| 2761 | s2 | SNP | 50% |
| 2762 | s2 | SNP | 50% |
| 2763 | s2 | SNP | 55% |
| 2764 | s2 | SNP | 40% |
| 2765 | s2 | SNP | 35% |
| 2766 | s2 | REF | 65% |
| 2767 | s2 | SNP | 45% |
| 2768 | s2 | SNP | 55% |
| 2769 | s2 | SNP | 55% |
| 2770 | s2 | SNP | 60% |
| 2771 | s2 | REF | 65% |
| 2772 | s2 | SNP | 60% |
| 2773 | s2 | REF | 60% |
| 2774 | s2 | SNP | 60% |
| 2775 | s45 | SNP | 40% |
| 2776 | s45 | REF | 45% |
| 2777 | s45 | REF | 45% |
| 2778 | s45 | SNP | 40% |
| 2779 | s45 | REF | 45% |
| 2780 | s45 | SNP | 40% |
| 2781 | s45 | SNP | 40% |
| 2782 | s45 | REF | 45% |
| 2783 | s45 | REF | 55% |
| 2784 | s45 | SNP | 45% |
| 2785 | s45 | REF | 50% |
| 2786 | s45 | REF | 45% |
| 2787 | s45 | REF | 45% |
| 2788 | s45 | REF | 50% |
| 2789 | s45 | SNP | 45% |
| 2790 | s45 | REF | 50% |
| 2791 | s45 | SNP | 45% |
| 2792 | s45 | REF | 50% |
| 2793 | s45 | SNP | 45% |
| 2794 | s45 | REF | 55% |
| 2795 | s45 | SNP | 50% |
| 2796 | s45 | REF | 50% |
| 2797 | s45 | SNP | 45% |
| 2798 | s45 | SNP | 40% |
| 2799 | s45 | REF | 45% |
| 2800 | s45 | SNP | 45% |
| 2801 | s45 | REF | 50% |
| 2802 | s45 | REF | 45% |
| 2803 | s45 | SNP | 40% |
| 2804 | s45 | SNP | 45% |
| 2805 | s45 | REF | 50% |
| 2806 | s45 | REF | 50% |
| 2807 | s45 | REF | 50% |
| 2808 | s45 | SNP | 45% |
| 2809 | s45 | REF | 50% |
| 2810 | s45 | SNP | 45% |
| 2811 | s45 | REF | 50% |
| 2812 | s45 | SNP | 50% |
| 2813 | s45 | REF | 55% |
| 2814 | s45 | REF | 55% |
| 2815 | s45 | SNP | 50% |
| 2816 | s45 | SNP | 45% |
| 2817 | s45 | SNP | 45% |
| 2818 | s45 | SNP | 45% |
| 2819 | s45 | REF | 50% |
| 2820 | s45 | REF | 50% |
| 2821 | s45 | SNP | 40% |
| 2822 | s45 | SNP | 45% |
| 2823 | s45 | SNP | 45% |
| 2824 | s45 | REF | 50% |
| 2825 | s45 | REF | 50% |
| 2826 | s45 | SNP | 45% |
| 2827 | s45 | REF | 55% |
| 2828 | s45 | SNP | 50% |
| 2829 | s45 | SNP | 45% |
| 2830 | s45 | REF | 50% |
| 2831 | s45 | REF | 50% |
| 2832 | s45 | SNP | 45% |
| 2833 | s45 | REF | 50% |
| 2834 | s45 | REF | 50% |
| 2835 | s45 | SNP | 45% |
| 2836 | s45 | SNP | 40% |
| 2837 | s45 | REF | 45% |
| 2838 | s45 | REF | 45% |
| 2839 | s45 | SNP | 40% |
| 2840 | s45 | REF | 50% |
| 2841 | s45 | SNP | 45% |
| 2842 | s45 | REF | 45% |
| 2843 | s45 | SNP | 40% |
| 2844 | s76 | SNP | 70% |
| 2845 | s76 | SNP | 50% |
| 2846 | s76 | SNP | 75% |
| 2847 | s76 | SNP | 60% |
| 2848 | s76 | SNP | 55% |
| 2849 | s76 | SNP | 70% |
| 2850 | s76 | SNP | 55% |
| 2851 | s76 | SNP | 50% |
| 2852 | s46 | SNP | 55% |
| 2853 | s46 | REF | 60% |
| 2854 | s46 | SNP | 60% |
| 2855 | s46 | REF | 65% |
| 2856 | s46 | SNP | 60% |
| 2857 | s46 | REF | 65% |
| 2858 | s46 | SNP | 65% |
| 2859 | s46 | REF | 70% |
| 2860 | s46 | SNP | 65% |
| 2861 | s46 | SNP | 60% |
| 2862 | s46 | REF | 65% |
| 2863 | s46 | SNP | 65% |
| 2864 | s46 | REF | 70% |
| 2865 | s46 | SNP | 65% |
| 2866 | s46 | SNP | 60% |
| 2867 | s46 | REF | 65% |
| 2868 | s46 | REF | 65% |
| 2869 | s46 | REF | 75% |
| 2870 | s46 | REF | 60% |
| 2871 | s46 | REF | 70% |
| 2872 | s46 | REF | 70% |
| 2873 | s46 | SNP | 65% |
| 2874 | s46 | REF | 65% |
| 2875 | s46 | REF | 70% |
| 2876 | s46 | SNP | 60% |
| 2877 | s46 | SNP | 60% |
| 2878 | s46 | SNP | 70% |
| 2879 | s46 | REF | 75% |
| 2880 | s46 | REF | 75% |
| 2881 | s46 | SNP | 70% |

TABLE 2-continued

Guide sequences designed to associate with specific SNPs of the GUCY2D gene

| SEQ ID NO: | SNP ID (Table 1) | Target (SNP/REF) | % GC |
|---|---|---|---|
| 2882 | s46 | REF | 65% |
| 2883 | s46 | SNP | 60% |
| 2884 | s46 | REF | 70% |
| 2885 | s46 | REF | 70% |
| 2886 | s46 | SNP | 70% |
| 2887 | s46 | REF | 75% |
| 2888 | s46 | REF | 75% |
| 2889 | s46 | SNP | 70% |
| 2890 | s46 | SNP | 70% |
| 2891 | s46 | REF | 75% |
| 2892 | s46 | REF | 75% |
| 2893 | s46 | SNP | 70% |
| 2894 | s46 | REF | 70% |
| 2895 | s46 | SNP | 65% |
| 2896 | s46 | REF | 65% |
| 2897 | s46 | REF | 65% |
| 2898 | s46 | SNP | 60% |
| 2899 | s46 | SNP | 60% |
| 2900 | s46 | SNP | 55% |
| 2901 | s46 | SNP | 65% |
| 2902 | s46 | REF | 70% |
| 2903 | s46 | SNP | 60% |
| 2904 | s46 | REF | 65% |
| 2905 | s46 | SNP | 60% |
| 2906 | s46 | REF | 65% |
| 2907 | s47 | REF | 75% |
| 2908 | s47 | SNP | 70% |
| 2909 | s47 | REF | 70% |
| 2910 | s47 | SNP | 65% |
| 2911 | s47 | SNP | 70% |
| 2912 | s47 | REF | 75% |
| 2913 | s47 | REF | 80% |
| 2914 | s47 | SNP | 75% |
| 2915 | s47 | SNP | 75% |
| 2916 | s47 | SNP | 75% |
| 2917 | s47 | REF | 75% |
| 2918 | s47 | SNP | 70% |
| 2919 | s47 | SNP | 70% |
| 2920 | s47 | REF | 75% |
| 2921 | s47 | SNP | 75% |
| 2922 | s47 | REF | 80% |
| 2923 | s47 | REF | 70% |
| 2924 | s47 | SNP | 65% |
| 2925 | s47 | SNP | 50% |
| 2926 | s47 | REF | 80% |
| 2927 | s47 | SNP | 75% |
| 2928 | s47 | REF | 75% |
| 2929 | s47 | REF | 55% |
| 2930 | s47 | SNP | 50% |
| 2931 | s47 | REF | 80% |
| 2932 | s47 | SNP | 75% |
| 2933 | s47 | SNP | 75% |
| 2934 | s47 | REF | 80% |
| 2935 | s47 | REF | 80% |
| 2936 | s47 | SNP | 75% |
| 2937 | s47 | SNP | 75% |
| 2938 | s47 | REF | 80% |
| 2939 | s47 | SNP | 60% |
| 2940 | s47 | REF | 80% |
| 2941 | s47 | REF | 65% |
| 2942 | s47 | SNP | 75% |
| 2943 | s47 | SNP | 75% |
| 2944 | s47 | REF | 80% |
| 2945 | s47 | SNP | 65% |
| 2946 | s47 | REF | 70% |
| 2947 | s47 | SNP | 75% |
| 2948 | s47 | REF | 80% |
| 2949 | s47 | SNP | 80% |
| 2950 | s47 | REF | 85% |
| 2951 | s47 | SNP | 60% |
| 2952 | s47 | REF | 85% |
| 2953 | s47 | SNP | 80% |
| 2954 | s47 | SNP | 75% |
| 2955 | s47 | REF | 80% |
| 2956 | s47 | REF | 65% |
| 2957 | s47 | SNP | 60% |
| 2958 | s47 | SNP | 75% |
| 2959 | s47 | REF | 80% |
| 2960 | s47 | REF | 80% |
| 2961 | s47 | SNP | 70% |
| 2962 | s47 | SNP | 75% |
| 2963 | s47 | REF | 55% |
| 2964 | s47 | SNP | 50% |
| 2965 | s48 | SNP | 65% |
| 2966 | s48 | REF | 70% |
| 2967 | s48 | SNP | 65% |
| 2968 | s48 | REF | 70% |
| 2969 | s48 | SNP | 65% |
| 2970 | s48 | SNP | 60% |
| 2971 | s48 | SNP | 65% |
| 2972 | s48 | REF | 70% |
| 2973 | s48 | SNP | 55% |
| 2974 | s48 | SNP | 55% |
| 2975 | s48 | SNP | 60% |
| 2976 | s48 | SNP | 55% |
| 2977 | s48 | SNP | 65% |
| 2978 | s48 | REF | 70% |
| 2979 | s48 | SNP | 65% |
| 2980 | s48 | SNP | 65% |
| 2981 | s48 | REF | 65% |
| 2982 | s48 | SNP | 55% |
| 2983 | s48 | SNP | 55% |
| 2984 | s48 | REF | 65% |
| 2985 | s48 | SNP | 60% |
| 2986 | s48 | SNP | 60% |
| 2987 | s48 | SNP | 60% |
| 2988 | s48 | REF | 65% |
| 2989 | s48 | SNP | 60% |
| 2990 | s48 | SNP | 55% |
| 2991 | s48 | REF | 60% |
| 2992 | s49 | SNP | 55% |
| 2993 | s49 | REF | 50% |
| 2994 | s49 | SNP | 65% |
| 2995 | s49 | REF | 60% |
| 2996 | s49 | SNP | 65% |
| 2997 | s49 | REF | 60% |
| 2998 | s49 | SNP | 50% |
| 2999 | s49 | REF | 45% |
| 3000 | s49 | REF | 55% |
| 3001 | s49 | SNP | 60% |
| 3002 | s49 | REF | 55% |
| 3003 | s49 | REF | 45% |
| 3004 | s49 | SNP | 50% |
| 3005 | s49 | SNP | 55% |
| 3006 | s49 | REF | 50% |
| 3007 | s49 | SNP | 60% |
| 3008 | s49 | SNP | 60% |
| 3009 | s49 | REF | 55% |
| 3010 | s49 | REF | 55% |

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Experimental Details

EXAMPLE 1

GUCY2D Correction Anaylsis

Guide sequences comprising 17-20 nucleotides in the sequences of 17-20 contiguous nucleotides set forth in SEQ ID NOs: 1-3010 are screened for high on target activity. On target activity is determined by DNA capillary electrophoresis analysis.

According to DNA capillary electrophoresis analysis, guide sequences comprising 17-20 nucleotides in the sequences of 17-20 contiguous nucleotides set forth in SEQ ID NOs: 1-3010 are found to be suitable for correction of the GUCY2D gene.

Discussion

The guide sequences of the present invention are determined to be suitable for targeting the GUCY2D gene.

REFERENCES

1. Ahmad and Allen (1992) "Antibody-mediated Specific Binging and Cytotoxicity of Lipsome-entrapped Doxorubicin to Lung Cancer Cells in Vitro", Cancer Research 52:4817-20
2. Anders (1992) "Human gene therapy", Science 256: 808-13
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200
4. Behr (1994) "Gene transfer with synthetic cationic amphiphiles: Prospects for gene therapy", Bioconjuage Chem 5:382-89
5. Blaese (1995) "Vectors in cancer therapy: how will they deliver", Cancer Gene Ther. 2:291-97
6. Blaese et al. (1995) "T lympocyte-directed gene therapy for ADA-SCID: initial trial results after 4 years", Science 270(5235):475-80
7. Buchschacher and Panganiban (1992) "Human immunodeficiency virus vectors for inducible expression of foreign genes", J. Virol. 66:2731-39
8. Burstein et al. (2017) "New CRISPR-Cas systems from uncultivated microbes", Nature 542:237-41
9. Chung et al. (2006) "Agrobacterium is not alone: gene transfer to plants by viruses and other bacteria", Trends Plant Sci. 11(1):1-4
10. Coelho et al. (2013) "Safety and Efficacy of RNAi Therapy for Transthyretin Amyloidosis", N Engl J. Med 369:819-29
11. Crystal (1995) "Transfer of genes to humans: early lessons and obstacles to success", Science 270(5235): 404-10
12. Dillon (1993) "Regulation gene expression in gene therapy" Trends in Biotechnology
13. Dranoff et al. (1997) "A phase I study of vaccination with autologous, irradiated melanoma cells engineered to secrete human granulocyte macrophage colony stimulating factor", Hum. Gene Ther. 8(1):111-23
14. Dunbar et al. (1995) "Retrovirally marked CD34-enriched peripheral blood and bone marrow cells contribute to long-term engraftment after autologous transplantation", Blood 85:3048-57
15. Ellem et al. (1997) "A case report: immune responses and clinical course of the first human use of ganulocyte/macrophage-colony-stimulating-factor-tranduced autologous melanoma cells for immunotherapy", Cancer Immunol Immunother 44:10-20
16. Gao and Huang (1995) "Cationic liposome-mediated gene transfer" Gene Ther. 2(10):710-22
17. Haddada et al. (1995) "Gene Therapy Using Adenovirus Vectors", in: The Molecular Repertoire of Adenoviruses III: Biology and Pathogenesis, ed. Doerfler and Bohm, pp. 297-306
18. Han et al. (1995) "Ligand-directed retro-viral targeting of human breast cancer cells", Proc Natl Acad Sci U.S.A. 92(21):9747-51
19. Inaba et al. (1992) "Generation of large numbers of dendritic cells from mouse bone marrow cultures supplemented with granulocyte/macrophage colony-stimulating factor", J Exp Med. 176(6):1693-702
20. Jinek et al. (2012) "A programmable dual-RNA-guided DNA endonuclease in adaptive bacterial immunity," Science 337(6096):816-21
21. Johan et al. (1992) "GLVR1, a receptor for gibbon ape leukemia virus, is homologous to a phosphate permease of Neurospora crassa and is expressed at high levels in the brain and thymus", J Virol 66(3):1635-40
22. Judge et al. (2006) "Design of noninflammatory synthetic siRNA mediating potent gene silencing in vivo", Mol Ther. 13(3):494-505
23. Kohn et al. (1995) "Engraftment of gene-modified umbilical cord blood cells in neonates with adnosine deaminase deficiency", Nature Medicine 1:1017-23
24. Kremer and Perricaudet (1995) "Adenovirus and adeno-associated virus mediated gene transfer", Br. Med. Bull. 51(1):31-44
25. Macdiarmid et al. (2009) "Sequential treatment of drug-resistant tumors with targeted minicells containing siRNA or a cytotoxic drug", Nat Biotehcnol. 27(7): 643-51
26. Malech et al. (1997) "Prolonged production of NADPH oxidase-corrected granulocyes after gene therapy of chronic granulomatous disease", PNAS 94(22):12133-38
27. Miller et al. (1991) "Construction and properties of retrovirus packaging cells based on gibbon ape leukemia virus", J Virol. 65(5):2220-24
28. Miller (1992) "Human gene therapy comes of age", Nature 357:455-60
29. Mitani and Caskey (1993) "Delivering therapeutic genes — matching approach and application", Trends in Biotechnology 11(5):162-66
30. Nabel and Felgner (1993) "Direct gene transfer for immunotherapy and immunization", Trends in Biotechnology 11(5):211-15
31. Remy et al. (1994) "Gene Transfer with a Series of Lipphilic DNA-Binding Molecules", Bioconjugate Chem. 5(6):647-54
32. Sentmanat et al. (2018) "A Survey of Validation Strategies for CRISPR-Cas9 Editing", Scientific Reports 8:888, doi:10.1038/s41598-018-19441-8
33. Sommerfelt et al. (1990) "Localization of the receptor gene for type D simian retroviruses on human chromosome 19", J. Virol. 64(12):6214-20
34. Van Brunt (1988) "Molecular framing: transgenic animals as bioactors" Biotechnology 6:1149-54
35. Vigne et al. (1995) "Third-generation adenovectors for gene therapy", Restorative Neurology and Neuroscience 8(1,2): 35-36
36. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78
37. Yu et al. (1994) "Progress towards gene therapy for HIV infection", Gene Ther. 1(1):13-26
38. Zetsche et al. (2015) "Cpf1 is a single RNA-guided endonuclease of a class 2 CRIPSR-Cas system" Cell 163(3):759-71
39. Zuris et al. (2015) "Cationic lipid-mediated delivery of proteins enables efficient protein based genome editing in vitro and in vivo" Nat Biotechnol. 33(1):73-80

SEQUENCE LISTING

The patent contains a lengthy sequence listing. A copy of the sequence listing is available in electronic form from the USPTO web site (https://seqdata.uspto.gov/?pageRequest=docDetail&DocID=US12168062B2). An electronic copy of the sequence listing will also be available from the USPTO upon request and payment of the fee set forth in 37 CFR 1.19(b)(3).

What is claimed is:

1. An isolated guide RNA (gRNA) that targets a mutant human guanylate cyclase 2D (GUCY2D) allele, wherein the gRNA comprises a CRISPR RNA (crRNA) consisting of the nucleic acid sequence of SEQ ID NO: 237, 238, 241, 242, 247, 248, 293, 294, 307, 413, 414, 417, 418, or 3011.

2. A method for inactivating a mutant GUCY2D allele, the method comprising:
   (a) delivering the gRNA of claim 1 and a CRISPR nuclease to an isolated human cell that comprises a mutant GUCY2D allele and a functional GUCY2D allele; and
   (b) culturing the cell obtained in step a) such that the mutant GUCY2D allele is inactivated, and the functional GUCY2D allele remains intact.

3. The method of claim 2, wherein the mutant GUCY2D allele is inactivated by a frameshift mutation.

4. The method of claim 3, wherein the frameshift mutation creates an early stop codon in the mutant GUCY2D allele.

5. The method of claim 3, wherein the frameshift mutation results in nonsense-mediated mRNA decay of a transcript of the mutant GUCY2D allele.

6. The method of claim 1, wherein the inactivated mutant GUCY2D allele expresses a truncated protein and the intact functional GUCY2D allele expresses a functional protein.

* * * * *